United States Patent [19]
Ryder et al.

[11] Patent Number: 5,705,365
[45] Date of Patent: Jan. 6, 1998

[54] KITS FOR DETERMINING PRE-AMPLIFICATION LEVELS OF A NUCLEIC ACID TARGET SEQUENCE FROM POST-AMPLIFICATION LEVELS OF PRODUCT

[75] Inventors: Thomas Brendan Ryder; Karen W. Shannon, both of Escondido; Daniel Louis Kacian, San Diego; Richard C. Harvey, San Diego; Sherrol H. McDonough, San Diego; Frank R. Gonzales, San Diego; Maria R. Castillo, Chula Vista; Elizabeth R. Billyard, San Diego; Nancy Lau Liu Shen, San Diego, all of Calif.

[73] Assignee: Gen-Probe Incorporated, San Diego, Calif.

[21] Appl. No.: 482,428

[22] Filed: Jun. 7, 1995

[51] Int. Cl.$^6$ .................... C12Q 1/68; C12P 19/34; C07H 19/00; C07H 21/02
[52] U.S. Cl. .................. 435/91.1; 435/6; 435/91.2; 536/22.1; 536/23.1; 536/24.3; 536/24.33; 536/25.32
[58] Field of Search .................. 435/6, 91.1, 91.2; 536/22.1, 23.1, 24.3, 24.33, 25.32

[56] References Cited

U.S. PATENT DOCUMENTS

| | | | |
|---|---|---|---|
| 4,683,195 | 7/1987 | Mullis et al. | 435/6 |
| 4,786,600 | 11/1988 | Kramer et al. | 435/235 |
| 4,946,958 | 8/1990 | Campbell et al. | 546/104 |
| 5,030,557 | 7/1991 | Hogan | 435/6 |
| 5,130,238 | 7/1992 | Malek et al. | 435/91 |
| 5,283,174 | 2/1994 | Arnold et al. | 435/6 |
| 5,399,491 | 3/1995 | Kacian et al. | 435/91.21 |
| 5,476,774 | 12/1995 | Wang et al. | 435/91.2 |

FOREIGN PATENT DOCUMENTS

| | | | |
|---|---|---|---|
| 0320308 | 6/1989 | European Pat. Off. . | |
| WO 91/02817 | 3/1991 | European Pat. Off. | C12Q 1/68 |
| 0497272 | 8/1992 | European Pat. Off. . | |
| 0525882 | 2/1993 | European Pat. Off. . | |
| 0587266 | 3/1994 | European Pat. Off. . | |
| 0587298 | 3/1994 | European Pat. Off. . | |
| 0623682 | 11/1994 | European Pat. Off. . | |
| 2691162 | 11/1993 | France . | |
| 9102818 | 3/1991 | WIPO . | |
| 9302215 | 2/1993 | WIPO . | |
| 9310257 | 5/1993 | WIPO . | |
| 9322461 | 11/1993 | WIPO . | |
| 9403472 | 2/1994 | WIPO . | |
| 9502067 | 1/1995 | WIPO . | |
| 9503430 | 2/1995 | WIPO . | |

OTHER PUBLICATIONS

Van Gemen, B.. "The One Tube Quantitative HIV-1 RNA NASBA. Precision Accuracy and Application", PCR Methods and Applications, vol. 4, 4:177–184, Feb. 1995.

Arnold, et al.. "PCR-based Quantitation Of Low Levels of HIV-1 DNA By Using An External Standard", Genetic Analysis Techniques and Applications, vol. 9 4:113–116, Aug. 1992.

Persing, D. In vitro Amplification Techniques. *Diagnostic Medical Microbiology: Principles and Applications*, Chp.3 at p. 65. (American Society for Microbiology; 1993 ed.).

Chelly, J., et al. Transcription of the dystrophin gene in human muscle and non-muscle tissues. 333 *Nature* 858–860 (1988).

(List continued on next page.)

*Primary Examiner*—Ardin H. Marschel
*Assistant Examiner*—Jezia Riley
*Attorney, Agent, or Firm*—Carlos A. Fisher

[57] ABSTRACT

Methods and kits for relating initial amounts of target nucleic acids present in a sample to target-specific amplification products. It has been discovered that the transcription-mediated amplification system is capable of producing a quantitative relationship between target input and target-specific output. Further, the the present invention relates to methods for carefully controlling this relationship resulting in an unexpectedly high degree of reproducability. Also described are useful methods for extending the dynamic range of transcription-based amplification systems.

42 Claims, 33 Drawing Sheets

2000 U T7 RNA polymerase per reaction:
T7 BH10 quantitative amplification using multiplex amplification format

OTHER PUBLICATIONS

Van Geme et al. A one-tube quantitative HIV-1 RNA NASBA nucleic acid amplification assay using electrochemiluminescent (ECL) labelled probes. 49 *J. Vir. Meth.* 157–168 (1994).

Modak & Marcus. Specific Inhibition of DNA Polymerase–Associated RNase H by DNA. 22 *J. Virol.* 243–246 (1977).

Marcus, et al. Reverse Transcriptase–Associated RNase H Activity. 27 *J. Virol.* 576–581 (1978).

Okayama, et al. High-Efficiency Cloning of Full-Length cDNA. 154 Methods Enzymol. 3–28 (1987).

Desrosiers, R. Virus Purification, Preparation of Infectious Virus Stock, and Virus Storage. *Techniques in HIV Research*, pp. 121–127, (Stockton Press, New York 1990).

10 U T7 RNA polymerase per reaction:
T7 BH10 quantitative amplification
using multiplex amplification format

5 U T7 RNA polymerase per reaction: T7 BH10 quantitative amplification using multiplex amplification format

75 U T7 RNA polymerase per reaction: T7 BH10 quantitative amplification using single amplicon format Summary of three T7 BH10 quantitative amplification experiments using single amplicon format Amplification of T7 BH10 standard for quantitation of HIV-1 viral lysate

Quantitative amplification of poly dT-selected HIV-1 lysate

Determination of number of HIV-specific RNA molecules per poly dT-selected HIV-1 lysate

Quantitative amplification of poly dT selected HIV-1 lysate, 1:10 dilution

Determination of number of HIV-specific RNA molecules per poly dT-selected HIV-1 lysate, 1:10 dilution

Quantitative amplification of poly dT-selected HIV-1 lysate, 1:100 dilution

Determination of number of HIV-specific RNA molecules per poly dT-selected HIV-1 lysate, 1:100 dilution

Summary of three experiments measuring number of HIV-specific RNA molecules in different dilutions of HIV-1 lysate

Effect of Lowering rNTP Concentration At 0.05 mM dNTPs $y = 785.401x^{0.936}$  $r^2 = 0.998$  □  2.0 mM rNTP $y = 163.435x^{0.989}$  $r^2 = 0.998$  ◇  0.5 mM rNTP

Effect of Lowering rNTP Concentration At 0.02 mM dNTPs

$y = 1123.838x^{0.924}$  $r^2 = 0.995$   □  1.0 mM rNTP $y = 866.556x^{0.872}$  $r^2 = 0.968$   ◇  0.5 mM rNTP

Effect of Lowering rNTP Concentration At 2.0 mM dNTPs $y = 139.634x^{0.981}$  $r^2 = 0.998$  ☐  1mM rNTP $y = 20.701x^{1.039}$  $r^2 = 0.990$  ◇  0.05mM rNTP

KITS FOR DETERMINING PRE-AMPLIFICATION LEVELS OF A NUCLEIC ACID TARGET SEQUENCE FROM POST-AMPLIFICATION LEVELS OF PRODUCT

FIELD OF THE INVENTION

This invention relates to methods for determining the pre-amplification levels of target nucleic acid molecules in a transcription-based isothermal amplification system. The invention is useful for determining the amount of RNA or DNA present in a given sample; for example, as a diagnostic tool or to monitor the results of treatment for a particular disease condition.

BACKGROUND OF THE INVENTION

This invention concerns procedures and techniques for determining the initial amount of a target nucleic acid present in a sample by subjecting the target nucleic acid to transcription-based nucleic acid amplification and relating the number of copies of amplified nucleic acid product to the amount of target nucleic acid present in the initial sample. The determination of the number of nucleic acid molecules of a given desired sequence (i.e., a target sequence) originally present in a sample is an increasingly important technique having numerous applications, including: diagnosis of a given disease or infection state, investigating genetic susceptibility to disease, predicting a patient's response to therapy, and measuring the response of a patient to various types of treatment against pathogens.

It will be understood that the term "target sequence" refers to a nucleic acid molecule having a given sequence of contiguous nucleotides as well as to nucleic acid molecules having the complementary sequence.

Nucleic acids belonging to biological entities can be specifically detected by nucleic acid hybridization. By "biological entities" is meant any replicating agent containing or consisting of nucleic acids, and depending on the replication of nucleic acids for its propagation. Thus the term "biological entities" includes higher and lower eukaryotes, prokaryotes, viruses, and viroids.

Typically in nucleic acid hybridization reactions a target nucleic acid is made single-stranded (if necessary), then reacted with a complementary probe oligonucleotide, usually linked to a detectable label, under conditions allowing the probe and target nucleic acid to anneal or "hybridize". The detectable label may be, without limitation, a radioactive atom such as $^{32}P$, or a light-emitting chemical moiety, such as a fluorescent, luminescent or chemiluminescent group, or an enzyme or enzyme substrate. By "complementary" is meant that at least a portion of consecutive nucleotide bases of one nucleic acid stand will hydrogen bond to a corresponding region of another nucleic acid stand under hybridization conditions. Hydrogen bonding usually occurs between adenine (A) and thymine (T) or uracil (U), or between guanine (G) and cytosine (C) nucleotide moieties. See e.g., Adams, et al., *The Biochemistry of the Nucleic Acids*, (11th ed., 1992).

Detection of the hybridized nucleic acid analyte is then accomplished by identifying completely or partially double-stranded (or sometimes multiple-stranded) nucleic acid molecules containing the probe. This often entails a physical separation step in which the double-stranded hybrid is isolated from other components; when the probe is labeled the separation step may involve isolating the labeled hybrid from the labeled free probe, and then detecting the hybrid-associated label as an indication of the presence of the nucleic acid analyte. Various methods including gel electrophoresis, column chromatography, and hydroxylapatite binding may be used to accomplish the physical separation.

Alternatively, or in conjunction with a physical separation step, the label may be differentially detectable in solution depending on whether the probe to which it is linked is free (unhybridized) or is involved in a double-stranded nucleic acid hybrid with the analyte. One such system, termed the hybridization protection assay (or HPA) and disclosed in Arnold et al., U.S. Pat. No. 5,283,174 (which enjoys common ownership with the present application and is incorporated by reference herein), is exemplified by the creation of microenvironmental conditions in which the label associated with a double-stranded nucleic acid is protected from degradation under conditions in which label associated with free probe undergoes hydrolysis. Thus, subsequent detection of the remaining label indicates the presence of the nucleic acid analyte in the sample.

Advantages to the use of nucleic acid hybridization in forensic, analytical, and diagnostic applications include the potential for high specificity of the nucleic acid hybridization reaction, the speed of the hybridization reaction under definable conditions, and the relative ease of performing hybridization assays. However, even when highly sensitive labels (such as some chemiluminescent labels) are used to detect nucleic acid analytes, analyte molecules present in a sample at copy numbers of less than about $2 \times 10^6$ cannot be detected using most "direct" hybridization tests.

In the last decade a number of methods for increasing the number of copies of nucleic acid molecules (or of molecules containing a given target nucleotide sequence) have been described. These methods are commonly known as nucleic acid amplification methods. The polymerase chain reaction (PCR) utilizes a DNA polymerase, primer molecules of opposite sense, and rounds of thermal cycling to cause the exponential replication of nucleic acid molecules; such a method is described in e.g., Mullis, et al., U.S. Pat. No. 4,683,195. Other amplification methods are the ligase chain reaction (LCR), EP 0 320 308; amplification methods utilizing a catalytic RNA to replicate nucleic acids, U.S. Pat. No. 4,786,600; amplification systems based on strand displacement, see Walker, et al., EP 0 497 272; and different transcription-based amplification methods. Among the latter are those of Malek, WO 91/02818; Kacian, et al., U.S. Pat. No 5,399,491; Kacian, et al., EP 0 587 266; and McDonough, et al., EP 0 587 298. The latter three of these references enjoy common ownership with the present invention and are incorporated by reference herein.

Amplification methods such as the foregoing permit the detection of small numbers of nucleic acid analyte molecules in a sample. For example, by conducting an amplification reaction and then using nucleic acid hybridization with a labeled probe to detect the amplified reaction products (amplicons), the presence of small numbers of a specific nucleic acid in a sample can be determined. Moreover, some amplification methods yield copies of the target sequence in quantities great enough to permit sequencing and/or cloning of the target-specific amplicon. However, nucleic acid amplification has not historically been a useful technique for obtaining information as to the number of target nucleic acids originally in a given sample.

Difficulties in using nucleic acid amplification as a method for determining the number of copies of a particular nucleic acid molecule in a given sample stem in part from the fact that, in many cases, nucleic acid amplification is an exponential process. See Persing, D., *In vitro Amplification Techniques* in *American Society for Microbiology, Diagnostic Medical Microbiology: Principles and Applications*, Ch. 3 at 65 (Persing et al., ed. 1993). As such, the results obtained from many amplification reactions have resembled an "all or nothing" or pseudo-quantum chemical reaction; for example, with low copy numbers of the target sequence the amplification reaction will fail to yield detectable amounts of the target sequence. However, past some critical target concentration most reactions will quickly yield very high numbers of target-specific amplicon. One initiated, most isothermal amplification reactions proceed so quickly that the rate of the reaction is not easily measured.

Other problems associated with determining the initial amount of the target sequence from the products of the amplification reaction can be traced to the particular amplification system used and its reaction kinetics, which, in turn, depend on its mechanism of amplification. Thus, the polymerase chain reaction (PCR), which utilizes a single enzyme and discrete cycles of amplification, might be expected to be a considerably more predictable system than systems requiring a greater number of enzymes or enzymatic activities. Systems such as PCR, having relatively greater simplicity than other amplification methods, would also be expected to be susceptable to more facile control than other multienzyme systems which operate in a more delicate equilibrium between different chemical reactions.

More generally, while the initial rate of many amplification reactions is exponential, even optimized isothermal amplification reactions finally reach a plateau at which the amplification reaction begins to slow, probably due, at least in part, to factors including the exhaustion of one or more of the reactants or limitation (e.g., by "enzyme death", target saturation, end product inhibition or other factors) of the catalytic components of the reaction (e.g., enzymes).

Furthermore, all nucleic acid amplification systems are susceptable to side reactions which compete with the desired amplification reaction. One such side reaction can be caused by the existence of non-target nucleic acids in the sample having stretches of contiguous nucleotides similar or identical to the primer-binding region of the target. A primer complementary to the target nucleic acid can form a transient mismatched hybrid with such a sequence; if the nucleic acid polymerase begins to extend the primer before it dissociates, the stability of the mismatched hybrid will be quickly increased due to hydrogen bonding to the point at which the primer will effectively fail to melt from the non-target nucleic acid.

These primer-extension products may be used in a subsequent step as templates for other primer extension reactions, so that what began as a non-specific "mismatch" can quickly result in the exponential propagation of non-target sequences having primer binding sites perfectly matched to the primers. Especially in cases where the target sequence is present in very low copy number amid a vast excess of non-target nucleic acid sequences, the products of the competing reactions can be the predominant products of the amplification reaction, effectively overwhelming the amplification of the target sequence with the result that amplification of the target is unpredictably suppressed to random degrees and may even fail to reach detectable levels.

Thus, the overall kinetics of a nucleic acid amplification reaction can, in some cases, only vaguely resemble the kinetics of amplification of the specific target nucleic acid. If only the final amount of target-specific amplicon is monitored, the results obtained may be misleading as to the efficiency of overall amplification and the sensitivity of the amplification reaction due to competitive side reactions.

Despite this, quantitative PCR amplification using internal standard nucleic acids has been described. For example, in Chelly, J., et al., 333 Nature 858–860 (1988) two different targets were coamplified (simultaneously amplified in the same reaction mixture) and radioactively labeled in the same PCR reaction mixture using different primer pairs, and the amounts of the resulting products were compared to obtain an estimated ratio of the starting materials; this experiment did not yield the absolute amount of starting material. No attempt was made in this case to ascertain that the amplification efficiencies of the two target sequences were similar. Product levels were estimated from the amount of radioactivity contained in each amplicon after gel electrophoresis.

In Griffiths, et al., WO 93/02215, a method of using a single primer set in conjunction with PCR to amplify both the target and control nucleotide sequences was disclosed. The control nucleotide sequence was identical to the target sequence except for the substitution of two nucleotides in the control sequence to create a diagnostic restriction site. The product amplicons were radiolabeled, subjected to restriction digestion, separated by gel electrophoresis and subjected to autoradiography. Amplicon bands were quantitated by scanning densitometry.

A similar method is disclosed in Pannitier, et al., WO93/10257. In this method, the control sequence and target sequences may differ in sequence or size by no more than 10%. After amplification by PCR, the resulting amplicons are detected either by using different labeled probes or by subsequent re-amplification with a new primer set yielding control and target amplicons of different sizes or having other identifiable characteristics.

Notably, in PCR methods each round of primer extension can theoretically be allowed to proceed long enough to ensure that virtually all the reaction products have produced. Thus, at least hypothetically, the amplification reaction can be allowed to go to completion at each step of the PCR procedure, resulting in a great degree of control over the PCR reaction. Notwithstanding this, it has been a common assumption that the exponential amplification of target nucleic acids in PCR might prevent it from being a quantitative procedure; see, Persing, supra.

By contrast to PCR, isothermal systems are more complex, continuous multienzyme systems in which, at any given moment, individual nucleic acid molecules are in different stages of the amplification process. Moreover, the specific mechanisms of the amplification process differ greatly among isothermal methods. While each such method is a means for obtaining information concerning the nucleotide sequence (including the presence or absence, amount or identity of the sequence) of a nucleic acid in a sample, different amplification methods are different chemical reactions which have distinctly different mechanisms. And although many of these methods may give rise to an exponential increase in the number of amplicons with increasing reaction time (at least for a limited time after initiation of the amplification process), the factors determining the reaction rate differ from method to method.

Anadeau, et al., EP 0 623 682, have disclosed the use of oligonucleotide control standards in strand displacement isothermal amplification (SDA) reactions in order to quantify pre-amplification levels of the coamplified target sequence. The oligonucleotide standards are coamplified with a sample having an unknown copy number of the target sequence. The internal control standards are amplified using the same primers used to amplify the target sequence, and have substantially the same length and G+C content as the target sequence.

Van Gemen, et al., EP 0 525 882, describe a method of quantitating the starting amount of target molecules using an isothermal transcription-based amplification system (NASBA™). In this method, a series of 5 identical reaction tubes containing equal amounts of the unknown nucleic acid were spiked with either 10, 100, 1,000, 10,000 or 100,000 copies of an internal standard, and the standard and target nucleic acids were coamplified. In this case, both the target nucleic acid and the standard were RNA and had identical base compositions; the standard RNA was designed to have a randomized or "scrambled" mutant version of the target nucleotide sequence. The amount of target RNA was defined as equal to the amount of added standard RNA in the reaction tube at which both target and mutant RNA amplicons were present in approximately equal amounts.

A variation of this method has been reported in Van Gemen, et al., 49 *J. Vir. Meth.* 157–168 (1994) in which three distinguishable randomized control RNAs are mixed in a single tube in differing amounts ($10^2$, $10^3$, and $10^4$ copies of standard) with the unknown sample, and the sample is coamplified with the standards. The amounts of unknown and standard amplicon are determined by using a set of probes, each specific to one of the four sequences, and the amount of amplified unknown RNA in the original sample then deduced by comparison with the standards. This method reportedly allows the quantification of nucleic acids over a 4 log range.

In the transcription-mediated isothermal amplification method, an embodiment of which is described in Kacian, et al., U.S. Pat. No. 5,399,491, two enzymes: a reverse transcriptase (RT) derived from a retrovirus, such as arian myeloblastosis virus (AMV) or Moloney murine leukemia virus (MMLV), and an RNA polymerase, are used in conjunction with one or more primers having a 5' sequence encoding a promoter sequence; this type of primer is termed a "promoter-primer". By "transcription-mediated amplification" is meant this two enzyme isothermal amplification system. By "transcription-based amplification" is meant any of a variety of isothermal amplification methods which utilize RNA transcription to achieve nucleic acid amplification.

In one possible format of transcription-mediated amplification, a promoter-primer hybridizes with an RNA target sequence and is extended by the RNA-directed DNA polymerase activity of the RT. The 3' end of the promoter-primer is extended by the DNA-directed DNA polymerase activity of the RT to create a double-stranded RNA:DNA hybrid. The RNAse H nicking and unwinding activities of RT then remove at least a part of the RNA template from the RNA:DNA hybrid and the resulting target-complementary DNA strand hybridizes with a primer of the same sense of the target. Extension of this primer results in the creation of a double-stranded promoter region. This promoter serves as a transcription initiation site for RNA polymerase, which uses the target complementary strand as a template to produce RNA transcripts, generally about 100–1000 copies thereof, containing the target sequence. Each of these transcripts is now available to begin the cycle anew. In some embodiments of this method, the extent of amplification can be up to $10^{12}$-fold or more.

It is important to note that there are significant differences between the retroviral reverse transcriptase-associated RNAse H activities and the RNAse H activites derived from cellular sources. For example, the cellular RNAse H enzymes, such as the RNAse H purified from *Escherichia coli*, are generally endonucleases having little or no base specificity with regard to their nucleolytic activity. These enzymes can be used in transcription-based nucleic acid amplification reactions at concentrations completely independent from the concentration of the DNA- and RNA-directed DNA polymerase activities.

However, in an embodiment of the amplification system described in Kacian, et al., U.S. Pat. No. 5,399,491 (previously incorporated by reference herein) the RNAse H activity of retroviral reverse transcriptase is the only source of RNAse H activity used in the reaction. Retroviral RNAse H activity displays preferences for endonucleolytic cleavage at specific bases or at loci having certain recognized base compositions. Id. Moreover, reverse transcriptase-associated RNAse H activity, being contained in the same enzyme as the DNA polymerase activities, is supplied at a constant concentration with respect to these activities, and can never be supplied at concentrations independent from RT in a two enzyme system. However, as mentioned below, conditions for optimal RT-associated RNAse H activity may not be the same as those for optimal RT activity.

In transcription-mediated amplification, the accumulation of the desired product can be dependent upon perhaps as many as five enzymatic activities (DNA-directed DNA polymerase, RNA-directed DNA polymerase, the nicking and unwinding activities of RNAse H, and RNA polymerase) functioning in a delicate equilibrium with each other. It would therefore be predicted that small changes in this equilibrium would lead to drastic variations in the amplification reaction. For example, if the first primer uses an RNA strand as the initial target, amplification can only occur if the RNA-directed DNA polymerase activity extends the primer (or 3' end of the template) at a greater rate than the RNAse H activity present in the reaction mixture, which causes dissociation of at least part of the RNA strand of the RNA:DNA double helix (and thus the primer binding site of the target amplicon). Since in the latter case the second promoter-primer has no template molecule to bind, the target sequence cannot be amplified.

Additionally, retroviral RNase H has been reported to be inhibited by DNA and single-stranded RNA; see Modak & Marcus 22 *J. Virol.* 243–246 (1977) and Marcus et al., 27 *J. Virol.* 576–581 (1978). Since the transcription-mediated amplification reaction described above produces large amounts of each (production of nucleic acids being the method's object), in light of these references one of ordinary skill would expect that hybrids created by extension of a DNA primer hybridized to an RNA template would accumulate in the amplification reaction with the result that the complementary primer would be unable to bind the (now double-stranded) primer extension product.

Thus, changes in the reaction conditions including the concentration of salts, concentrations or source of enzymatic activities, reaction temperature, or the addition or accumulation of compounds, such as pyrophosphate, which might inhibit or stimulate one or more enzymatic activities (among other factors) would be expected to shift the reaction equilibrium, or otherwise change the reaction, in unpredictable ways.

As described above, and in contrast to PCR in which the extent of amplification is susceptable to control by the number and length of temperature cycles, in transcription-mediated amplification individual molecules exist in different stages of the amplification process at a given time. Thus, the exponential kinetics of the overall amplification reaction represent an "averaging" of the kinetics for each of the individual stages in the process.

As a result, the rate of product accumulation in this assay may also be influenced by factors such as the rate of hybridization of the primers to their targets, the rate of enzyme binding and the turnover rates of the enzymes used, in addition to the factors mentioned above. Because of this, the dynamic range and the amplification extent are inherent properties of a given amplification system and the target and primers used in that system.

There exists a need in the art for methods of determining the initial amount of a target nucleic acid in a sample subjected to transcription-based nucleic acid amplification in general, and in transcription-mediated amplification in particular. Specifically, it is desirable that such an amplification method be capable of displaying a reproducable, quantitative relaionship between input target level and output signal (target-specific amplicon). The relationship must be predictable across a wide range of target concentrations, preferably the range will encompass target concentrations across greater than 3 orders of magnitude, more preferably across grater than 4 orders of magnitude.

There also exists a need for such methods in which this reproducable relationship holds at low target input levels (e.g., 100 copies and less).

Preferably, the amount of output target-specific amplicon should lie in a range which is directly measurable without the need for dilution of the reaction mixture in order to avoid contamination, both of the reaction with nucleases and of the laboratory with the amplification products.

SUMMARY OF THE INVENTION

The present invention is related to methods for determining the starting number of copies of a given target sequence in a nucleic acid amplification reaction.

In the present invention the Applicants have shown that the transcription-mediated amplification system is capable of producing a quantitative relationship between target input and target-specific output. Further, the Applicants have shown that under carefully controlled conditions this relationship shows an unexpectedly high degree of reproducability. Still further, in certain embodiments Applicants have invented useful methods for extending the dynamic range of transcription-based amplification systems.

In one aspect of the present invention Applicants have surprisingly found that it is possible to extend the period during which the amplification reaction (i.e. accumulation of target sequence product) remains in an exponential, predictably measurable rate of increase. Additionally, in aspects of the invention, reaction conditions are made submaximal, resulting in either or both an extension of the reproducable dynamic range of the assay or adjustment of the extent of the amplification reaction.

By "submaximal" is meant that the reaction conditions are altered from those yielding the the greatest amount of product for a given target and primer set combination. Thus, a qualitative amplification system will normally be designed to yield the greatest possible amount of signal (target-specific amplicon) for a given target. Applicants have discovered that these maximized conditions are often not optimal for achieving quantitative amplification.

It has been found that, even in cases in which the dynamic range of the amplification reaction is not extended, amplification under submaximal conditions results in a reproducable correlation between target input levels and target-specific product levels when amplification is conducted under defined conditions. Morerover, in cases where extreme sensitivity is not necessary, a suboptimal amplification can allow accurate detection of higher initial target levels (depending on the desired target reange to be detected) without resort to dilution of the product samples.

In a preferred aspect of the present invention, reaction conditions are made submaximal by reducing the concentration of a single enzyme, RNA polymerase, in the reaction mixture. Under these conditions the amount of target in the starting sample can be determined with a high degree of accuracy and with high sensitivity over a reproducable dynamic range in a multiplex amplification format (simultaneous amplification of more than one different amplicon). Moreover, using the methods of the present invention in a "single amplicon" format, the reproducable dynamic quantifiable range of the amplification can be extended to 6–8 logs, with a precision of between 0.3 and 0.2 logs or less. Furthermore, using this preferred embodiment, less than 10 initial copies of the target sequence can be quantified. It is important to note that increasing the dynamic range is a different concept than reduction of the extent of the amplification reaction, which may occur under submaximal conditions in certain embodiments of the present invention without increasing the dynamic range of the reaction.

By "dynamic range", "reproducable dynamic range", "reproducable response", or "reproducable dose response" is meant that the increase in the log of the product concentration is a reproducable function of the log of the pre-amplification number of copies of the target sequence originally in the sample for otherwise identical amplification reactions.

In another aspect, the reaction conditions are made submaximal by altering the ability of a promoter-primer to initiate RNA transcription of the target sequence. In one embodiment of the invention, the promoter sequence of the promoter-primer is altered through the introduction of one or more base substitutions or deletions to reduce the number of RNA transcripts produced by the RNA polymerase. As an illustration, Applicants have found that alteration of the T7 promoter by substitution of the adeneine at the −6 position (the 16th base of SEQ ID NO:9) of the promoter sequence with a cytosine or a guanine, or by substitution of the adenine at the −10 position (the 12th base of SEQ ID NO:9) with a cytosine can reproducably reduce the extent of amplification allowing product levels to fall within the range of detection at higher target input levels.

In a related embodiment, the primer-binding portion of the promoter primer may contain base substitutions or insertions, extra bases, or deletions which cause the promoter-primer to bind the RNA template less strongly than would otherwise be the case; this renders the amplification reaction submaximal.

In other embodiments, the reaction conditions are made submaximal by lowering the reaction temperature. For example, Applicants have found that varying the reaction temperatures by as little as 4° C. can cause between 100 and 1000 times less product to be made under otherwise identical conditions.

In yet other embodiments, Applicants have found that by modulating the concentration of cofactors necessary for the amplification reaction, such as $Mg^{++}$, the extent of the amplification reaction can be reproducably altered. By conducting amplification under two or more concentrations of magnesium ion, the relationship of input target nucleic acid to target-specific amplicon produced can be maintained over a wider range of input concentrations than would otherwise be the case.

In addition to the amplification reaction itself, another factor influencing the ease or possibility of detecting target sequence in the original sample is related to the method of detection of target-specific products. While some of the described methods for quantification of absolute copy numbers of target sequence involve the use of gel electrophoresis and/or radioactive labeling of the probes used to detect the products of amplification, disadvantages to such detection methods include their cost, the required level of skill in the handling of toxic or radioactive materials, the need for specialized facilities and permits for toxic waste disposal, increased danger of amplicon-caused contamination of the laboratory.

Applicants preferably detect the amplification products using probes joined to chemiluminescent labels; a preferred class of such labels are the acridinium ester derivatives. Acridinium ester labels are described in Campbell, et al., U.S. Pat. No. 4,946,958, incorporated by reference herein. The acridinium ester derivatives are preferably used by the Applicants in an assay format termed the hybridization protection assay (HPA), disclosed in Arnold, supra, previously incorporated by reference herein. In this system, the amount of chemiluminescence is measured in relative light units (RLU) in a luminometer. Applicants preferably use either a LEADER® 450 or a LEADER® 50 luminometer (Gen-Probe Incorporated, San Diego, Calif.). This detection system has the advantages that it is rapid and easy to use, requires no extraordinary safety precautions, may be performed in solution, and is extremely sensitive as compared to methods employing gel electrophoresis and/or radioactivity.

Photomultiplier tubes used in commercial luminometers used in clinical and research laboratories for detection of luminescent labeling compounds have inherent limitations in their dynamic range, in that the response to RLU input of the instruments may tend to become saturated at RLU values exceeding $1.5-2.0 \times 10^6$. Such limitations are independent of questions pertaining to dynamic range of nucleic acid amplification. In addition to the methods for precisely controlling the amplification reaction disclosed herein, Applicants have devised methods for bringing the quantitative information from the nucleic acid amplification reaction within the dynamic range of the luminometer. Such methods include submaximal amplification, altering the specific activity of the probe used to detect the target-specific amplicons, serial dilution of the products of amplification and increasing the $T_m$ of the probe by shortening it, raising the hybridization temperature. These methods can also be combined with other methods described herein to obtain quantification of the initial copy number of a given target sequence.

Therefore, it is an object of the present invention to provide a highly accurate and reproducible method of determining the absolute and/or relative pre-amplification number of a target nucleic acid sequence in a sample from the amplification products of an amplification reaction. It is also an object of the invention to provide means for extending the dynamic range of a transcription-based nucleic acid amplification method by altering the reaction kinetics of the amplification reaction without sacrificing sensitivity or reproducibility of the amplification method.

It is further an object of the present invention to provide methods for determining the number of copies of a target nucleic acid sequence present in a sample, from detection and measurement of the products of the amplification reaction, in situations in which the initial copy number of the target nucleic acid sequence is between about 1 to $10^9$ copies, preferably between about 10 to $10^8$ copies; more preferably between about $10^2$ to $10^8$ copies, between about $10^2$ to $10^7$ copies and between about $10^2$ to $10^6$ copies.

It is further an object of the invention to provide methods for the quantification of specific nucleic acid sequences in a sample by utilizing an external standard to establish a standard curve plotting the extent of a transcription-based amplification reaction as a function of the number of absolute copies of a target nucleotide sequence in the starting sample. By comparing the standard curve with the extent of amplification of the target sequence in samples in which the number of such sequences is unknown, the absolute number of copies of the target sequence in the "unknown" samples can be determined.

In some embodiments of the present invention, it is contemplated that quantification of the pre-amplification copy number of a target sequence will be accomplished without the use of competitive coamplification of the target sequence and one or more internal standard. Nevertheless, Applicants also foresee that the methods described herein may be used in conjunction with such coamplification methods. In such a case, the target sequence and the nucleotide sequence of the internal standard should be independently distinguishable while having similar or identical amplification efficiencies. Due to the unique mechanism of transcription-based amplification methods, the major product of each "cycle" of the amplification reaction is RNA. Because RNA has a significant tendency to form secondary structures through intramolecular hydrogen bonding, far greater than single-stranded DNA, designing internal standard nucleotide sequences having approximately the same amplification efficiency as the target sequence presents difficulties far different from those present in a DNA-based amplification system such as PCR. Design strategies such as merely randomizing the nucleotide sequence of the target sequence do not assure that the internal standard(s) will have a similar amplification efficiency as the target sequence under the same reaction conditions.

Thus, another object of the present invention is to provide methods of determining the pre-amplification copy numbers of a target sequence by altering the dynamic range of the amplification reaction, using internal standards substantially similar to the target sequence. One such method utilizes an internal standard sequence having identical or similar G+C base content and with a nucleotide sequence identical to the target sequence except for a subsequence of between one and five bases which permits independent detection of target and standard amplicons following the amplification reaction, for example by using the HPA format described above. Preferably both target and standard sequences should be amplified using the same primers.

DETAILED DESCRIPTION OF THE INVENTION

Figure 1A:
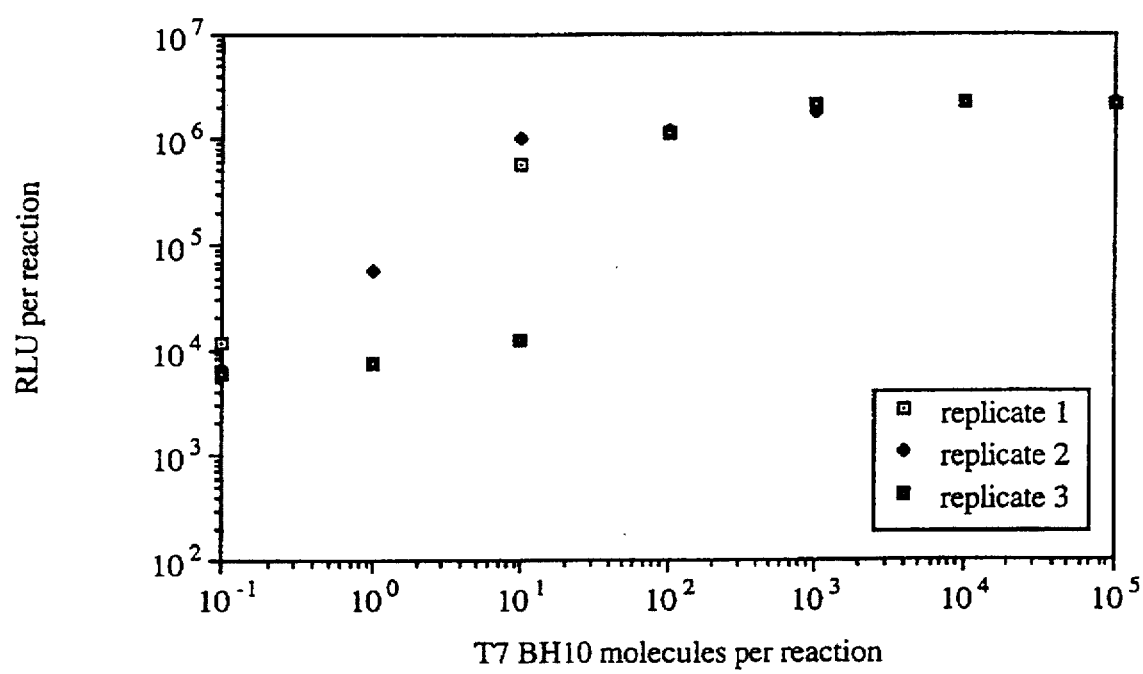
FIGS. 1A through 1F contains plots of the amount of target-specific amplicon produced in a multiplex transcription-mediated amplification reaction as a function of initial target amount, in which T7 RNA polymerase levels are varied between 2,000 units and 5 units per reaction. Reactions were run in triplicate for each point.
Figure 1B:
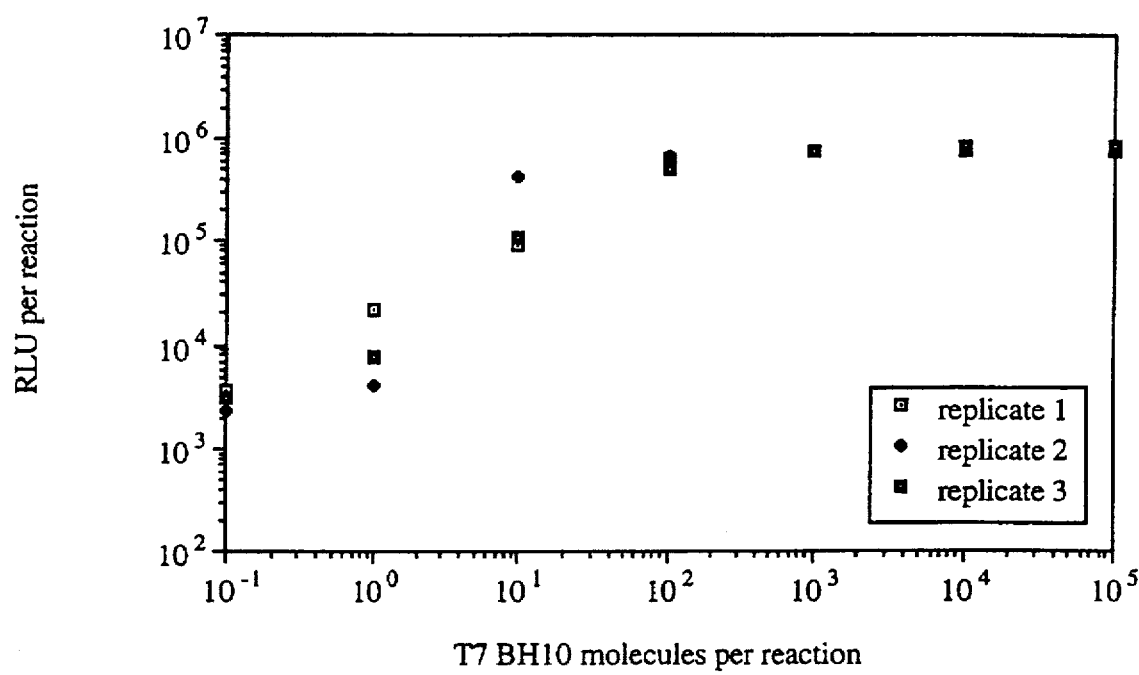

Applicants have discovered methods for determining the pre-amplification copy number of a target sequence from the number of target sequence-containing amplicons produced by transcription-based amplification reactions in general and transcription-mediated amplification in particular. These methods were made possible by the surprising discovery that the creation of submaximal reaction conditions preferably by a reduction in the concentration of a single catalyst, RNA polymerase, can cause the extension of the reproducable dynamic range of the amplification reaction to between 4 and 6–8 logs.

By contrast, a reduction in the levels of another enzyme used in the reaction, reverse transcriptase, does not result in an extension of the dynamic range. However, such a reduction may be useful for creating submaximal conditions in cases where sensitivity of the amplification reaction is not crucial.

Applicants have also invented methods combining this technique with means for causing the amount of detected target-specific amplicons produced in the amplification reaction to fall within the reproducable range of the detection system used. One such method utilizes combinations of labeled and unlabeled target-specific probes of identical sequence to detect the desired amplification product. These combinations contain different ratios of labeled probe to unlabeled probe; a single amplification reaction is carried out and the reaction products are assayed using probe mixtures of different specific activities.

Transcription-based amplification methods such as the ones described herein utilize five enzyme activities: RNA polymerase, DNA-directed DNA polymerase, RNA-directed DNA polymerase and nicking and unwinding RNAse H activities, to cause the exponential increase of nucleic acid molecules containing a target nucleotide sequence. In the transcription-mediated amplification method described as an embodiment of Kacian et al., U.S. Pat. No. 5,399,491, the RNAse H activities are contained in a retroviral reverse transcriptase. In one possible format utilizing this method, a primer hybridizes with an RNA target sequence and is extended by the RNA-directed DNA polymerase activity. The RNAse H activities then at least partially remove the RNA template from the RNA:DNA hybrid and the resulting target-complementary DNA strand hybridizes with a promoter-primer of the same sense as the target. The 3' end of the target-complementary strand is extended by the DNA-directed DNA polymerase activity to create a double-stranded promoter region; the 3' end of the promoter-primer may also be extended. The RNA polymerase uses the target complementary strand as a template to produce RNA transcripts containing the original target sequence. Each of these transcripts are now available to bind a new primer molecule, and so forth. In another format, the first primer to bind to the target is a promoter-primer. In still other embodiments of this amplification method the initial target molecules are DNA rather than RNA.

EXAMPLES

The following examples serve to describe various embodiments of the present invention. The examples shall not be construed as limiting the invention to these embodiments, said invention being defined solely by the claims concluding this specification and equivalents thereof.

Example 1

The RNA used in these examples was a 8935 base transcript of the plasmid pGEM3ZfHIV(+). This plasmid contains the SstI restriction fragment of HIV BH10-R3 DNA between bases 36 and 9153 of the HIV genome. This restriction fragment was cloned into the plasmid pGEM®-3Zf(+) (Promega Corporation, Madison, Wis.) immediately downstream from a T7 promoter sequence. Prior to transcription, the isolated plasmid was linearized by restriction digestion at the unique XbaI site, located immediately downstream from the 3' end of the HIV coding strand. Transcripts containing the target sequence were prepared in 50 mM Tris-HCl (pH 7.6), 1.75 mM MgI$_2$, 25 mM KCl, 2 mM spermidine, 2.5 mM each of CTP and UTP, 6.5 mM ATP and GTP, 2000 units of T7 RNA polymerase and approximately 10 µg of linearized DNA template in a total volume of 100 µl. The reaction mixture was incubated for 60 minutes at 37° C. Cloning and in vitro transcription procedures are well known in the art and are described in e.g., Sambrook, et al., *Molecular Cloning: A Laboratory Manual* (Cold Spring Harbor Laboratory Press, 2nd ed., 1989) which is hereby incorporated by reference.

RNA transcripts were purified by centrifugation through a cesium trifluoroacetate gradient as described in Okayama et al. 154 *Methods Enzymol.* 3 (1987), incorporated by reference herein, precipitated in ethanol, and centrifuged to pellet the precipitated RNA. The supernatant was discarded, and the RNA pellet was resuspended in 500 µL 10 mM HEPES (N-[2-hydroxyethyl]piperazine-N'-[2-ethanesulfonic acid]) (pH 7.5), 1 mM EDTA.

The target RNA, termed BH10 RNA, was diluted in the same buffer to a final concentration of 8.3×10$^7$ molecules/µL, and the resulting stock solution was stored in single-use aliquots at −80° C.

Multiplex Amplification Format

In this example two different regions of the target RNA transcript were amplified simultaneously in a transcription-mediated amplification system.

A lyophilized preparation containing 37.5 µmol ATP and GTP, 15 µmol CTP and UTP, 300 µmol Tris-Cl (pH 8.0), 0.6 µmol desferoxamine mesylate, 12 µmol spermidine trihydrochloride, 1.5 nmol of a primer of SEQ ID NO:1, 0.75 nmol of a promoter-primer containing SEQ ID NO:2, 0.15 nmol of a primer of SEQ ID NO:3, 0.15 nmol of a promoter-primer containing SEQ ID NO:4, 0.3 nmol of a primer of SEQ ID NO:5, 2.4 nmol of a primer of SEQ ID NO:6, 0.6 nmol of a promoter-primer containing SEQ ID NO:7, 2.4 nmol of a promoter-primer containing SEQ ID NO:8, 1.2 nmol dNTPs, and 120 mg polyvinylpyrrolidone (PVP) was reconstituted in 1.5 mL of a solution containing 0.3% (v/v) ethanol, 20% (v/v) glycerol, 50 mM MgCl, 0.02% (w/v) methyl paraben, 0.01% (w/v) propyl paraben, 0.6 mM zinc acetate, and 70 mM KCl. Promoter-primers are disclosed in e.g., Kacian & Fultz, U.S. Pat. No. 5,399,491, previously incorporated by reference. The 5' end of each promoter-primer contained a T7 promoter sequence of SEQ ID NO:9.

Twenty-five microliters of the resulting solution was dispensed to separate 12×75 mm polypropylene tubes. Target RNA was added, in 50 µL nuclease-free water, to tubes at average target levels of 0.1, 1, 10, 10$^2$, 10$^3$, 10$^4$, and 10$^5$ copies per tube; this series was prepared in triplicate. A triplicate set of tubes containing no target RNA was also prepared as a negative control.

Moloney murine leukemia virus reverse transcriptase (MMLV-RT)(United States Biochemicals Inc., Cleveland, Ohio; 75 U/µL) and T7 RNA polymerase (Epicentre Technologies, Madison, Wis.) were diluted into a solution containing 40 mM HEPES (pH 7.5), 0.6 mM EDTA, 125 mM N-acetyl-L-cysteine (NALC), 0.1 mM zinc acetate, 90 mM KCl, 0.2 M trehalose, 0.2% (v/v) of TRITON X-102, 0.001% (w/v) phenol red, 20% (v/v) glycerol. Each reaction tube contained 2000 units of MMLV-RT, and different amounts of T7 RNA polymerase were added to each reaction tube as indicated below.

One unit of MMLV-RT is defined as equal to the amount of enzyme required to synthesize 1 fmol of single-stranded cDNA in 15 minutes at 37° C. One unit of T7 RNA polymerase is defined as equal to the amount of enzyme required to synthesize 1 fmol of RNA in 20 minutes at 37° C.

The samples to be amplified and primers were incubated at 60° C. for 6 minutes, then cooled to 42° C. for two minutes before the addition of the enzyme solution. Twenty microliters of the enzyme solution containing the appropriate amounts of MMLV-RT and T7 RNA polymerase were added to each tube, and the tubes incubated at 42° C. for 90 minutes. The tubes were then transferred to 60° C. for 10 minutes to terminate the reactions.

Target-specific amplicons were detected and quantified using the hybridization protection assay (HPA), disclosed in Arnold, supra, previously incorporated by reference herein. Oligonucleotide probes had the sequences SEQ ID NO: 10, SEQ ID NO:11, and SEQ ID NO:12 and were labeled with 4-(2-succinimidyloxycarbonyl ethyl)-phenyl-10-methylacridinium-9-carboxylate fluorosulfonate (hereafter referred to as "standard AE") linked via a non-nucleotide linker to the oligonucleotide probe. See Arnold, et al., EP 0 313 219, supra, previously incorporated by reference. Additionally, an unlabeled helper probe having SEQ ID NO:13 was used to facilitate binding of probe in these experiments. Helper probes and their use in facilitating binding of labeled probes are disclosed in Hogan, U.S. Pat. No. 5,030,557, which enjoys common ownership with the present application and which is incorporated by reference herein.

One hundred microliters of a probe solution containing 1 mM mercaptoethanesulfonic acid, 0.4 nM of each probe, 20 nM of the unlabeled helper probe, 100 mM succinic acid, 230 mM lithium hydroxide, 20 mM EDTA, 20 mM ethylene glycol bis (beta-amino ethyl ether) N, N, N$^1$, N$^1$ tetraacetic acid (EGTA), 73 mM lithium lauryl sulfate, 1.2M lithium chloride and 15 mM aldrithiol was added to each amplification tube. Probes were allowed to hybridize to their targets for 15 minutes at 60° C. Three hundred microliters of a hydrolysis solution containing sodium borate (pH 8.5) and 1.0% (v/v) TRITON® X-100 were added to each reaction tube and the tubes incubated for 10 minutes further at 60° C. The remaining chemiluminescence was measured in a luminometer upon the addition of 200 µL of a 0.1% (v/v) H$_2$O$_2$ in 1 mM HNO$_3$ followed immediately with the addition of 200 µL of a solution containing 1M NaOH. The results are reported in relative light units (RLU), which is a measure of the number of photons emitted by the chemiluminescent label used.

The results are shown in graphical format in FIGS. 1A–1F. Each of these figures show the results of three identical replicate experiments. Furthermore, FIGS. 1A–1F show the results of the addition to each reaction mixture of 2000, 50, 20, 15, 10 and 5 units of T7 RNA polymerase, respectively; the reaction mixtures were otherwise identical. Both the x- and y-axis of each plot are logarithmic.

These results show that at high levels of RNA polymerase (e.g., 2000 units) the amplification response for this target region and primer set is essentially an "all or none" phenomenon. Thus, FIG. 1A shows that at average target levels of 1 target molecule per reaction, signal above background was seen in one of the three replicate reactions; the signal obtained from the other two replicates was not significantly above background levels, presumably due to stochastic variability in the number of target molecules in each reaction. At average target levels of 10 target molecules per reaction, two of the three replicate reactions had reached a maximum level of signal, indicating very high product levels.

Figure 1C:
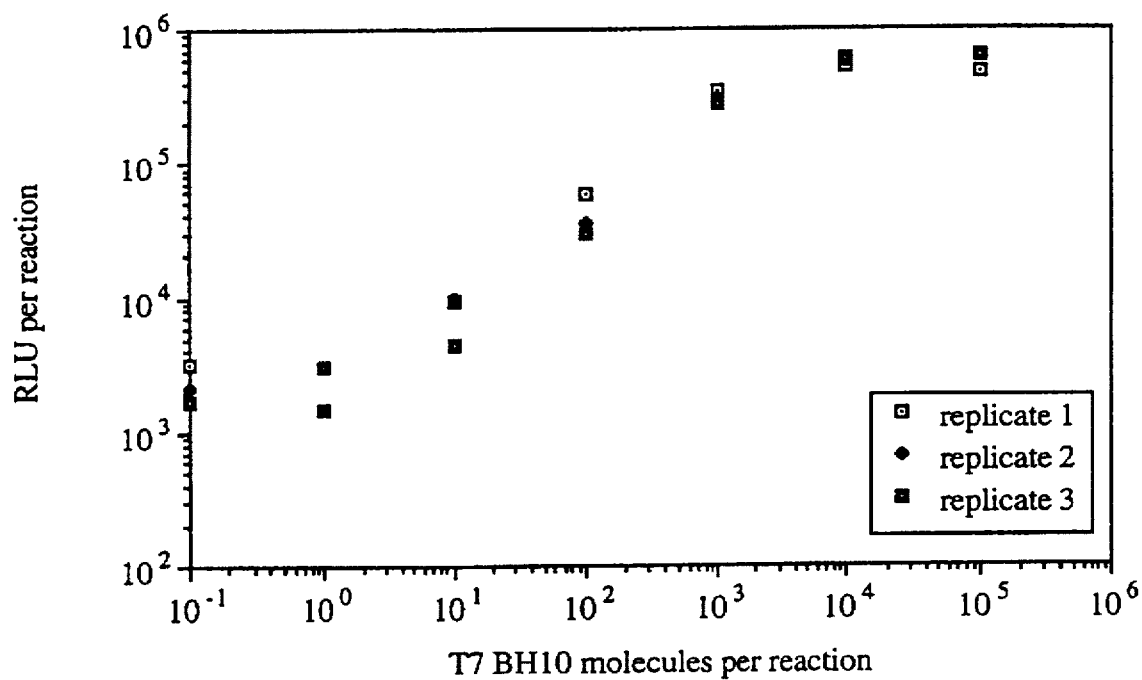
Figure 1D:
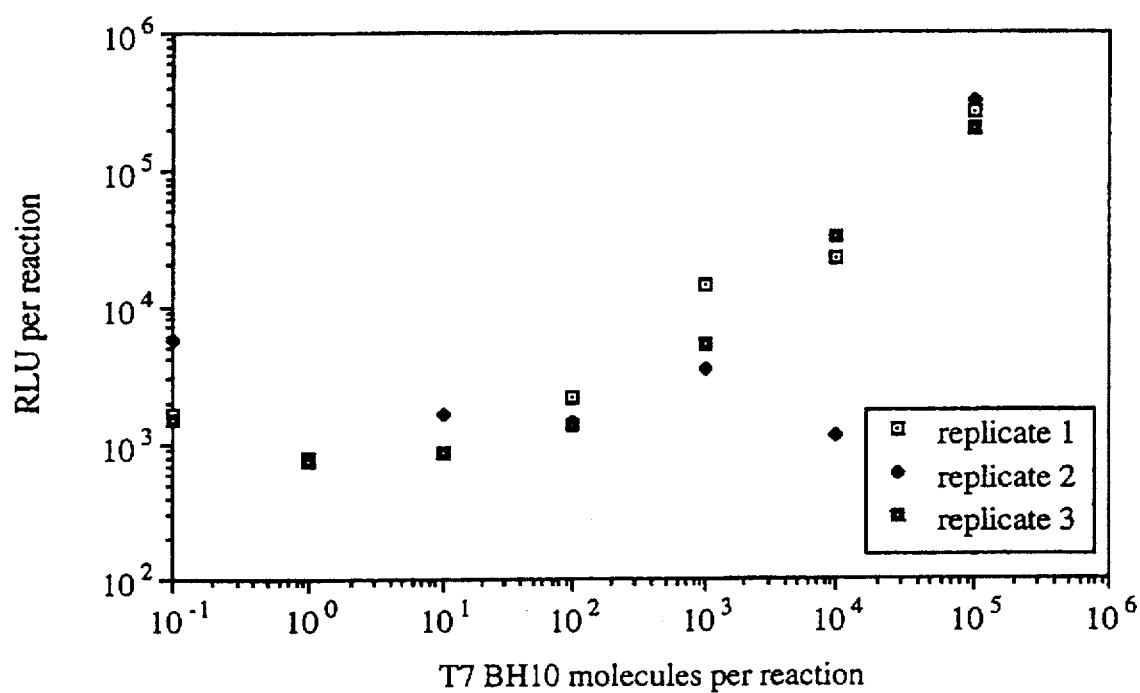
Figure 1E:
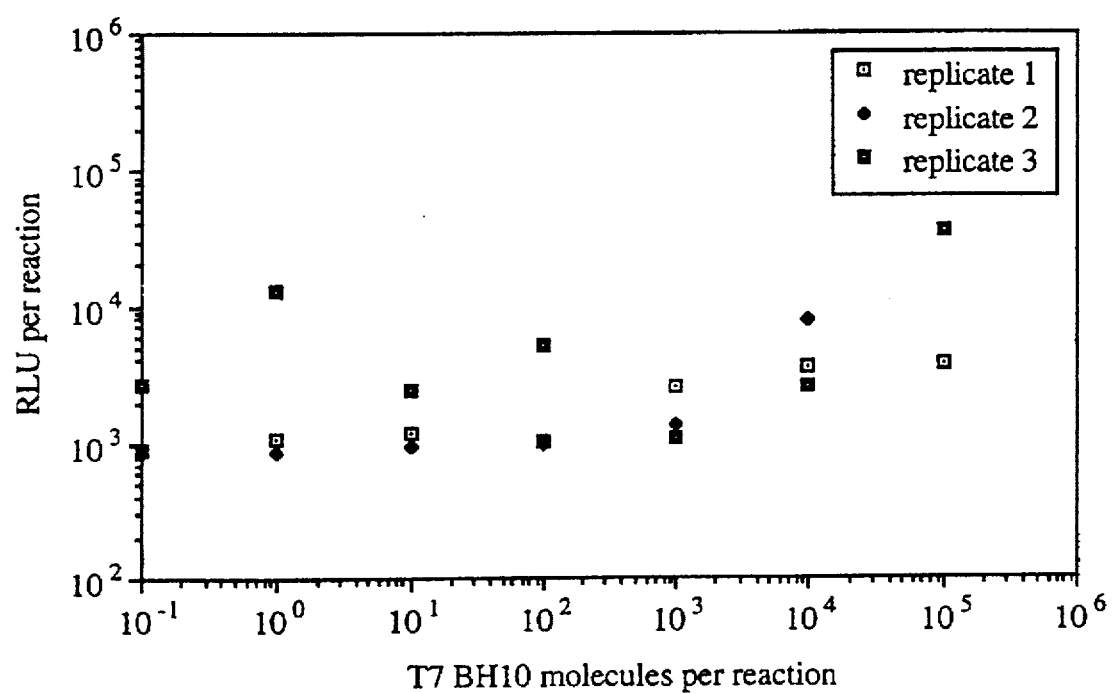
Figure 1F:
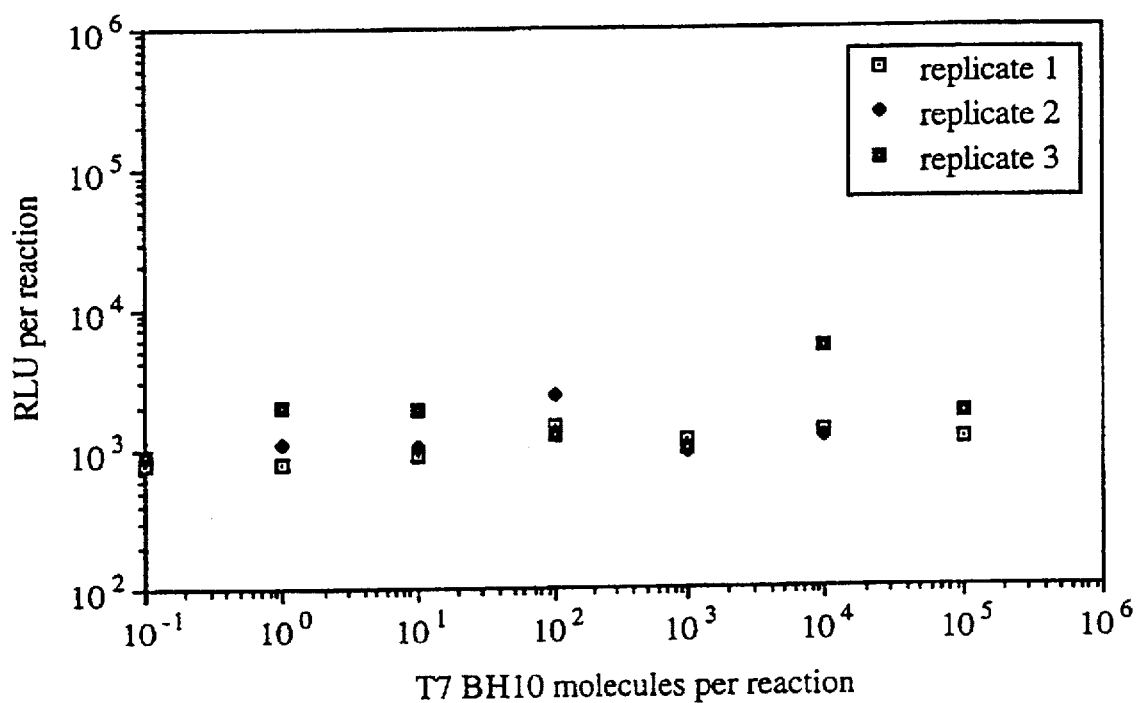
Figure 2A:
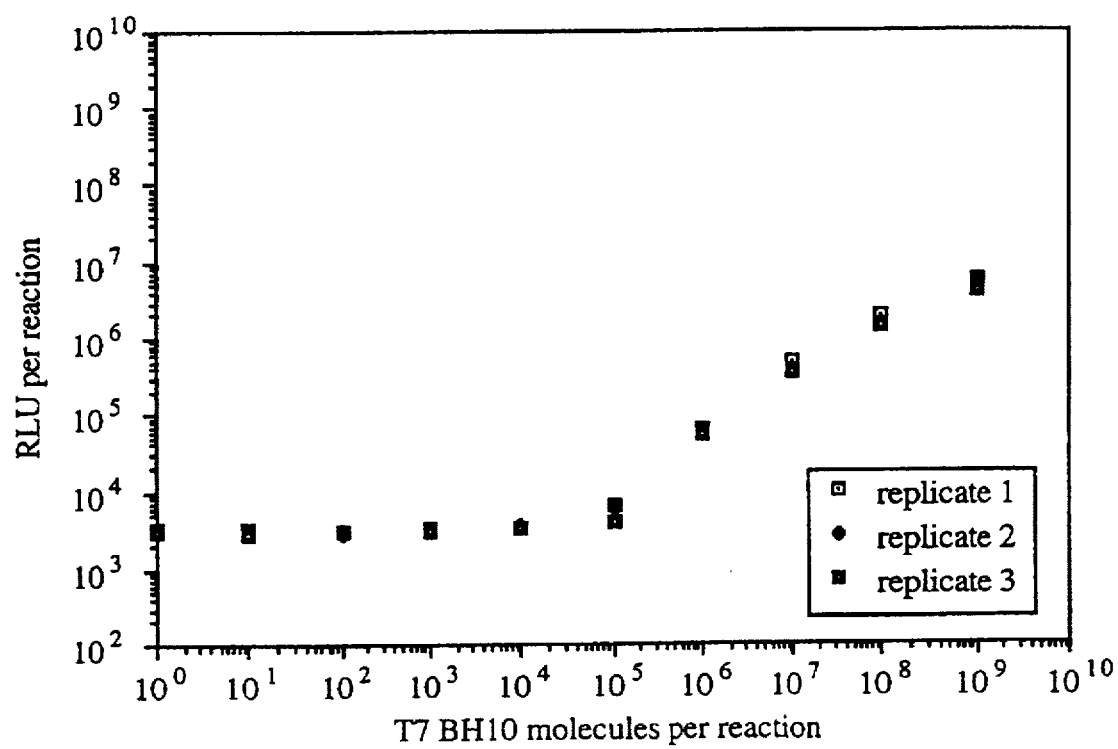
FIGS. 2A through 2D contains plots of the amount of target-specific amplicon produced in a single amplicon transcription-mediated amplification reaction as a function of initial target amount, in which T7 RNA polymerase levels are varied between 100 and 25 per reaction. Reactions were run in triplicate for each point.
Figure 2B:
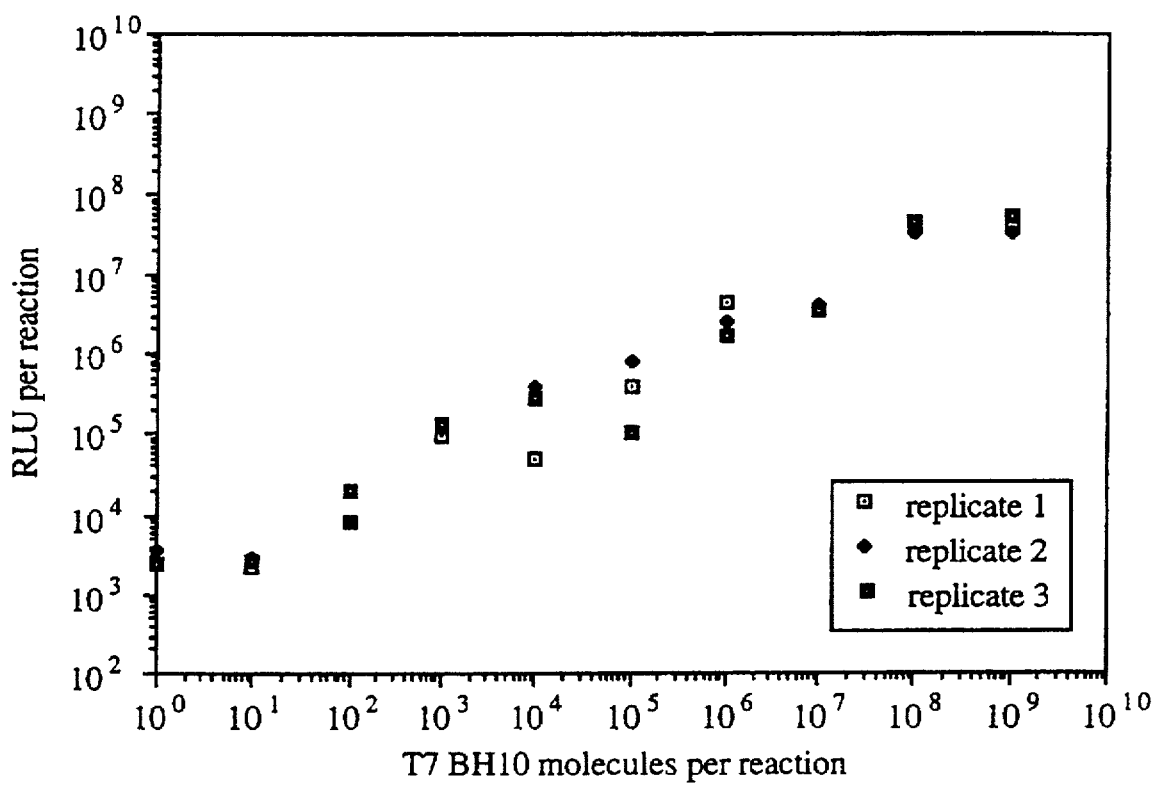
Figure 2C:
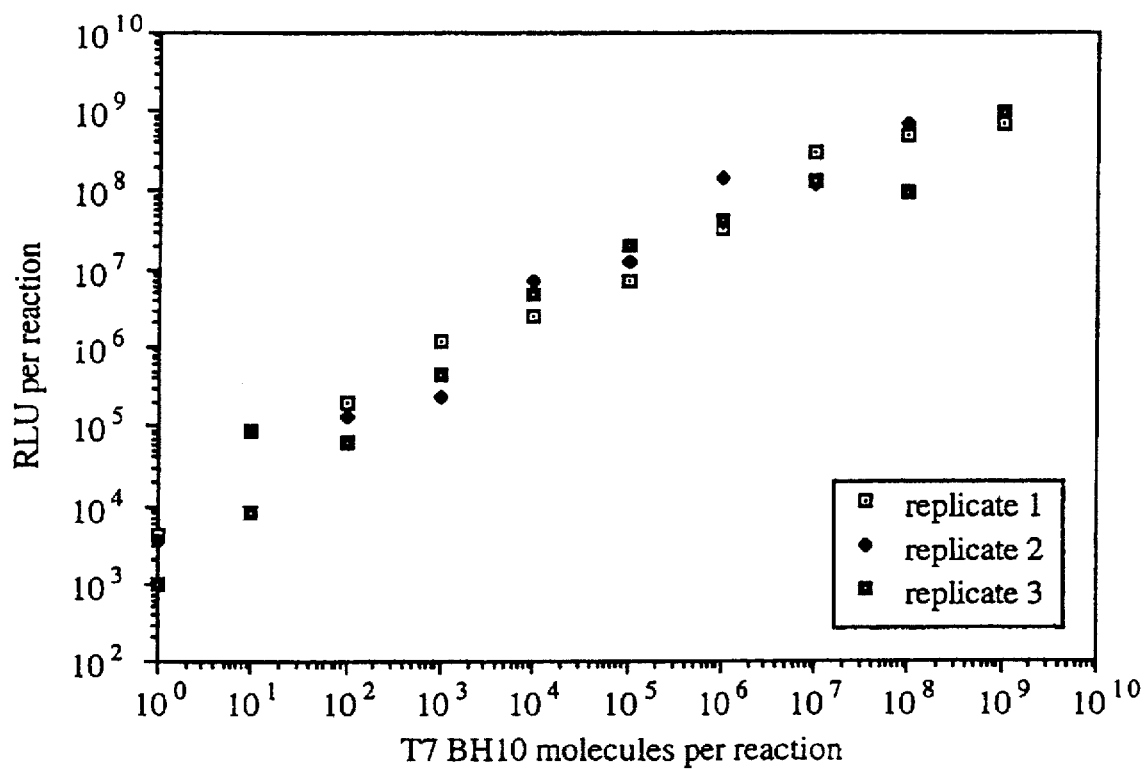
Figure 2D:
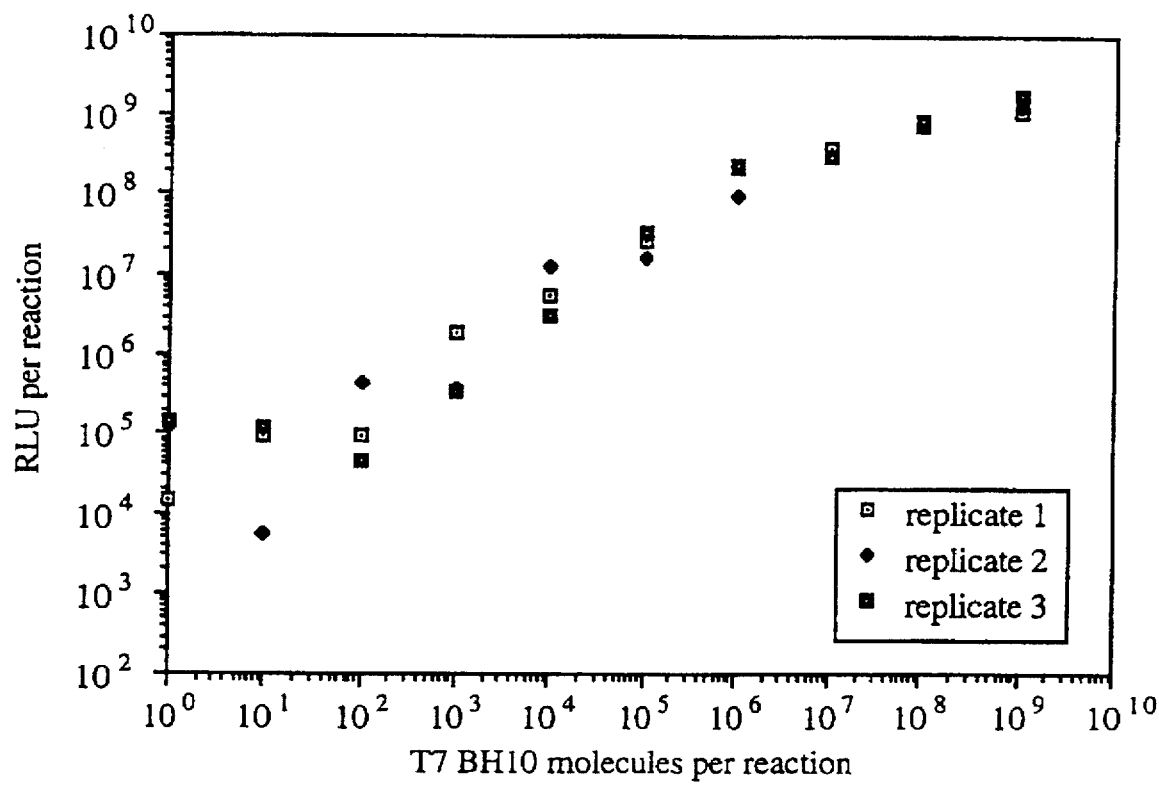

As the amount of T7 RNA polymerase in the amplification is reduced, the variability among replicates is reduced and the reproducable dynamic range of the amplification is broadened. Reactions containing 50 units of T7 RNA polymerase (FIG. 1B) showed a linear dose response between 1 and 10 molecules; however, the variation (e.g., standard deviation) in the amount of signal obtained in replicate tubes was significantly decreased. Both the linear dose response and increased precision of the amplification reaction was optimal in this multiplex amplification system at RNA polymerase levels of between 15 and 20 units per reaction (FIGS. 1C and 1D). Under these conditions, linearity of the assay was between 2 and 3 logs of initial target: between 10 and 1,000 average copies for the experiment illustrated in FIG. 1C, and between about 1,000 and 100,000 average copies for the experiment illustrated in FIG. 1D. Due to limitations in the luminometers used to monitor the quantity of amplification products, combined with the background chemiluminescence in the assay, an effective linear dose response between 2 and 3 logs of light emission (RLU) is observed in this experiment. This can be seen in FIG. 1. As shown in the following example, techniques such as diluting the amplified, probe-hybridized amplification products can extend the reproducable dynamic range over an even greater range.

At levels of RNA polymerase of 10 units per reaction (FIG. 1E), the variability of replicate reactions has increased; additionally, no amplification response is seen in reactions containing average target levels of 10,000 or less. Finally, at RNA polymerase levels of 5 units per reaction, the reactions do not demonstrate response over background at any of the average target input levels attempted.

Example 2

Single Amplicon Format

In this experiment, a single target sequence was amplified using four primers: two promoter-primers and two non-promoter primers, as is disclosed in Ryder et al., WO 95/03430, to enhance the effectiveness of target-specific initiation, and thus sensitivity of the amplification reaction at low target levels. This application enjoys common ownership with the present invention and is incorporated by reference herein.

The amplification reactions were set up as follows. A lyophilized preparation identical to that described in Example 1, but not containing primers having SEQ ID NOs:5, 6, 7 and 8, was reconstituted in 1.5 mL of a solution containing 0.3% (v/v) ethanol, 20% (v/v) glycerol, 50 mM MgCl, 0.02% (w/v) methyl paraben, 0.01% (w/v) propyl paraben, 0.6 mM zinc acetate, and 70 mM KCl. Twenty-five microliters of the resulting solution was dispensed to separate 12×75 mm polypropylene tubes. Target RNA was added, in 50 μL nuclease-free water, to tubes at average target levels of 0.1, 1, 10, $10^2$, $10^3$, $10^4$, $10^5$, $10^6$, $10^7$, $10^8$, and $10^9$ copies per tube; this series was prepared in triplicate. A triplicate set of tubes containing no RNA was also prepared as a negative control.

Moloney murine leukemia virus reverse transcriptase (MMLV-RT)(United States Biochemicals Inc., Cleveland, Ohio) and T7 RNA polymerase (Epicentre Technologies, Madison, Wis.) were diluted into a solution containing 40 mM HEPES (pH 7.5), 125 mM N-acetyl-L-cysteine, 0.6 mM EDTA, 0.1 mM zinc acetate, 0.2% TRITON X-102, 0.2M trehalose, 20%(v/v) glycerol, 90 mM KCl, and 0.001%(w/v) phenol red. The samples to be amplified, in separate tubes, were incubated at 60° C. for 6 minutes, then cooled to 42° C. for two minutes before the addition of the enzyme solution. Twenty microliters of the enzyme solution containing 2000 units of MMLV-RT and the amount of T7 RNA polymerase indicated in the figure was added the reaction tubes, and the tubes incubated at 42° C. for 90 minutes. The tubes were then transferred to 60° C. for 10 minutes to terminate the reactions.

Detection of the reaction products was performed as above, with the following exceptions. The labeled probe had SEQ ID NO:1. The unlabeled helper probe had SEQ ID NO:4. Additionally, ten-fold serial dilutions of the products of each amplification reaction were made in nuclease-free water prior to inducing chemiluminescence to ensure that the emitted light from each tube fell within the linear range of the detection system used. One hundred microliters of the diluted reaction products from each reaction were given 100 μL of the probe reagent, which contained 4 nM of each labeled probe and 200 nM of the unlabeled helper probe. The hybridization protection assay was conducted as in Example 1.

The results are plotted in FIG. 2A–2D. As can be seen, at RNA polymerase levels of 25 units per reaction (FIG. 2A) a linear amplification was observed at average initial target levels of 100,000 copies and greater. Furthermore, at this RNA polymerase level, the assay shows a linear dynamic range over at least 3 logs, between $10^6$ copies and $10^9$ copies of target, the highest target level tested.

At RNA polymerase levels of 50 units per reaction (FIG. 2B) or 75 units per reaction (FIG. 2C), the reproducable dynamic range of the assay is expanded to at least 6–7 logs (between about 100 average copies of target and $10^8$ average copies of target for reactions containing 50 units of T7 RNA polymerase, and $10$–$10^8$ average copies of target for reactions containing 75 units of T7 RNA polymerase). The variation of replicate samples also appears to be quite small, especially at RNA polymerase levels of 75 units per reaction.

At RNA polymerase levels of 100 units per reaction, the variation between samples has increased. Moreover, the range of average target levels at which the reaction has a linear dynamic range is less than was true in FIGS. 2B and 2C; about 5 logs. The effect of the T7 RNA polymerase concentration on the dynamic range of the amplification reaction conducted in this example is summarized below.

| T7 RNA POLYMERASE (UNITS) PER REACTION | DYNAMIC RANGE OF AMPLIFICATION REACTION |
|---|---|
| 25 | $10^6$ target copies to $10^9$ target copies |
| 50 | $10^2$ target copies to $10^8$ target copies |
| 75 | $10^1$ target copies to $10^7$ target copies |
| 100 | $10^2$ target copies to $10^7$ target copies |

Note the difference between the dynamic range of the assay under the conditions of amplifying a single amplicon and the dynamic range of assays conducted under the multiplex amplification conditions of Example 1. Note also that the target sequence of Example 2 is a subset of a target sequence of Example 1; thus it is appropriate to compare the results of the two experiments since the experiments had primers, probes, reaction conditions and reaction time in common. Note also that as the T7 RNA polymerase concentration decreases, the extent of amplification decreases also at all tested target concentrations.

Lastly, the combined results of Examples 1 and 2 clearly suggest that the optimal concentration of RNA polymerase to achieve reproducablity in this amplification system differs depending on factors including the number of amplicons to be amplified in the same reaction, the primers used, and the target sequence to be amplified. Accordingly, it would be well within the ability of one of ordinary skill in the art to determine the optimal concentration of RNA polymerase to expand the dynamic range of the transcription-based amplification of a given target sequence using this specification as a guide.

Example 3

Figure 3A:
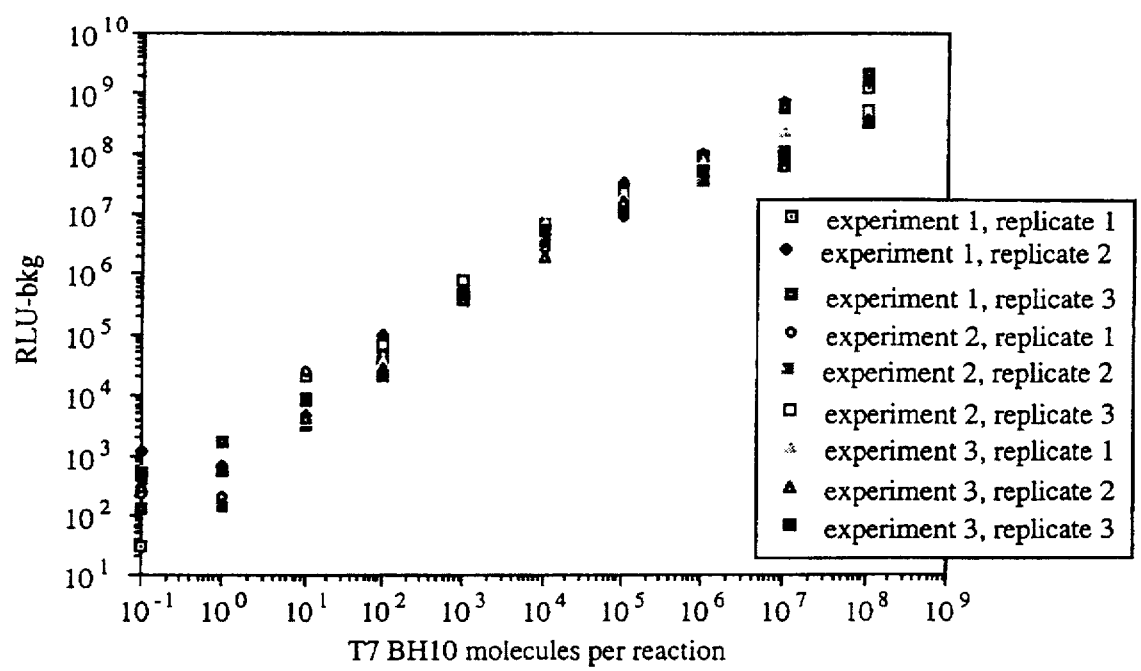
FIGS. 3A through 3C contains plots summarizing three separate experiments and correlating the amount of target-specific amplicon produced in a multiplex transcription-mediated amplification reaction to initial target amount. In each experiment, reactions were run in triplicate for each point.
Figure 3B:
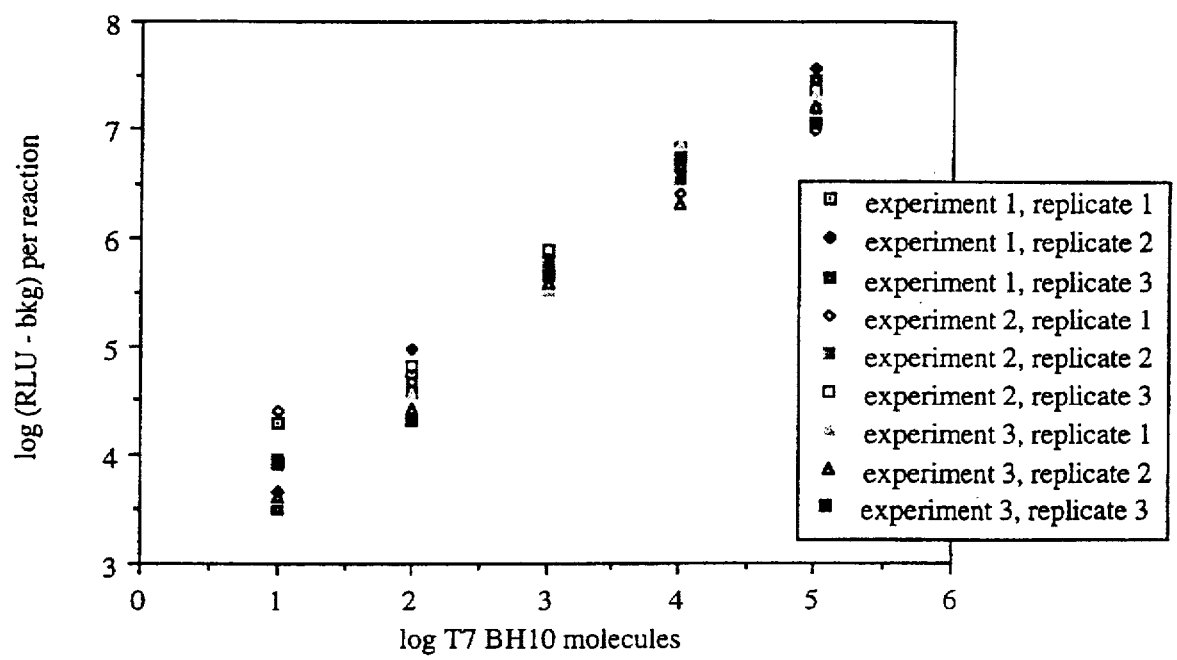
Figure 3C:
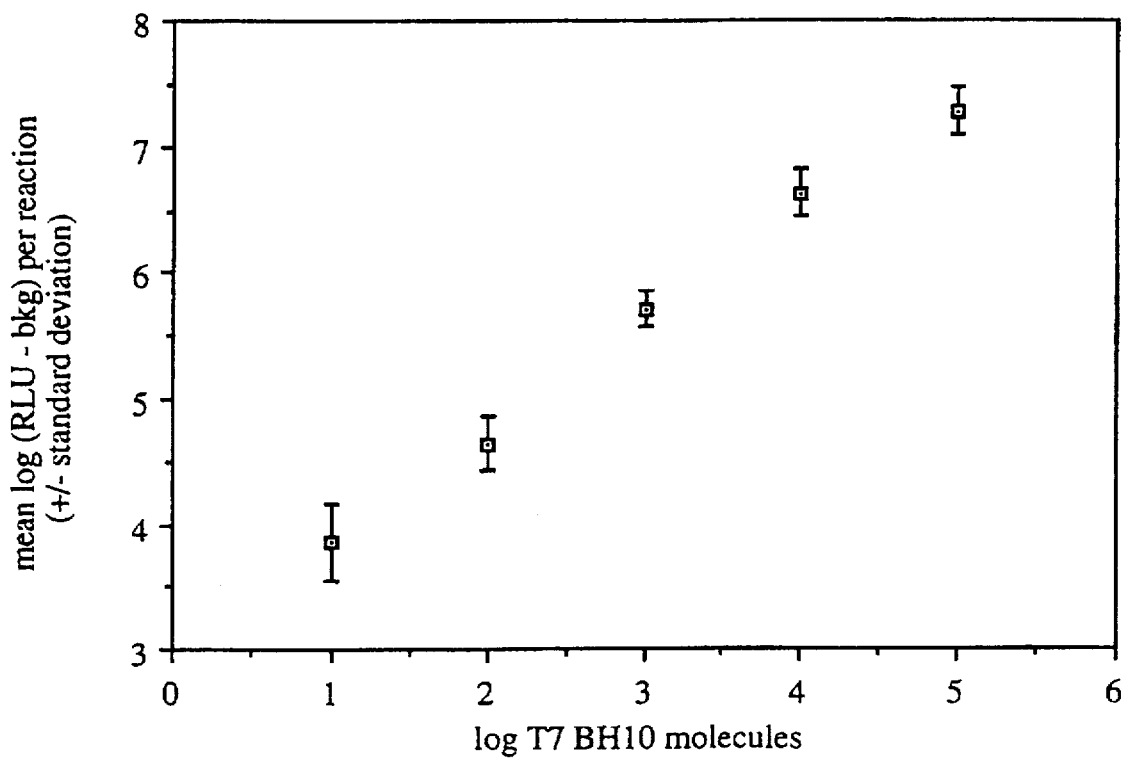

Nucleic acid amplification was performed as in Example 2, using $10^{-1}$, $10^0$, $10^1$, $10^2$, $10^3$, $10^4$, $10^5$, $10^6$, $10^7$, and $10^8$ molecules of the BH10 target RNA and with 75 units of T7 RNA polymerase per reaction tube. As in Example 3, the amplification products were diluted prior to hybridization with labeled probe and detection of the label. Three replicate reactions were conducted for each target level. Additionally, this experiment was repeated twice more on different days to test the precision of the quantitative assay. The results are shown below and in FIG. 3A–3C; the standard deviation and C.V. calculations represent 9 data points per target level. FIG. 3B is an enlargement of the data presented in FIG. 3A plotting the portion of these same data covering from 10 to 100,000 average initial target copies which represents the reproducable dynamic range of the assay. FIG. 3C summarizes the mean and standard deviation calculations of the data below. All graphs are log/log plots.

| AVERAGE NUMBER OF COPIES TARGET RNA | LOG NET MEAN RLU (RLU MINUS BACKGROUND) | STANDARD DEVIATION | COEFFICIENT OF VARIABILITY (CV) |
|---|---|---|---|
| $10^8$ | 8.803 | 0.3167 | 3.60% |
| $10^7$ | 8.275 | 0.4290 | 5.18% |
| $10^6$ | 7.798 | 0.1564 | 2.01% |
| $10^5$ | 7.276 | 0.1864 | 2.56% |
| $10^4$ | 6.637 | 0.1834 | 2.76% |
| $10^3$ | 5.708 | 0.1371 | 2.4% |
| $10^2$ | 4.647 | 0.2089 | 4.50% |
| $10^1$ | 3.873 | 0.3096 | 7.99% |

The results of this experiment show that within much of the reproducable range of the assay the precision of replicate samples is 0.2 log or less, and the standard deviation never exceeds 0.43 logs. At low target levels (such as 10 molecules and less) greater variability is expected, due to stochastic considerations.

Thus, the methods of the present invention provide means for determining and verifying the initial number of target molecules from the amount of amplification products over a broad range of initial target levels. Additionally and unexpectedly, the invention also provides means for increasing the precision of the assay itself, leading to increased confidence in the results obtained and increased assay sensitivity.

Example 4

Assay of HIV Viral Lysates Using a Single Amplicon Format

HIV vital RNA was isolated as follows. RNA was extracted from HIV strain HIV-1 MN infectious virus stock prepared as described by R. Desrosiers in *Techniques in HIV Research*, A. Aldovini and B. D. Walker (eds.), pp 121–127, Stockton Press, New York 1990) by vigorously mixing 100 μL virus stock (having a titer of 11,900 syncytia-forming units/mL) with 900 μL of a solution containing 50 mL HEPES (pH 7.5), 5% lithium lauryL sulfate, 500 mM lithium chloride and 10 mM EDTA. Two ten-fold serial dilutions of the viral lysates (final 10× and 100× dilutions) were made before proceeding to the next step.

Poly-adenylated RNA was isolated from each dilution of the lysate in triplicate, by adding 30 μL of oligo(dT) 25-coated magnetic beads (Dynal P/N 610.05) to 100 μL lysate and the suspensions were incubated for 5 minutes at room temperature to allow hybridization of polyadenylated HIV RNA to the beads. The beads were then collected using a magnet and washed once in 10 mL HEPES (pH 7.5), 150 mM sodium chloride, 0.1% sodium lauryl sulfate, and 1 mM EDTA and twice in 10 mM HEPES (pH 7.5), 1 mM EDTA, 150 mM NaCl, 0.5% TRITON® X-100. Finally, the beads were resuspended in 1.0 mL nuclease-free water and the suspensions were stored on ice until amplification.

Figure 4A:
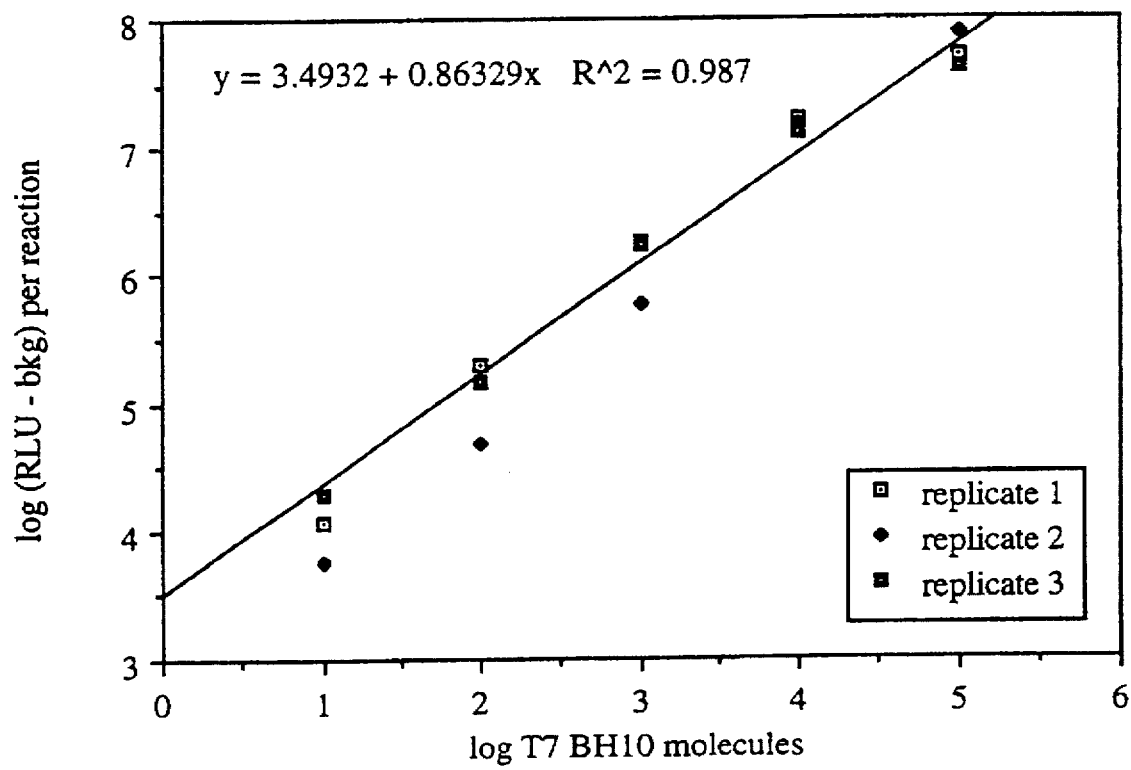
FIGS. 4A through 4C illustrate, respectively, a standard curve generated for quantitation of HIV RNA levels in viral lysates, a graph showing the amount of signal obtained in each of three experiments performed in triplicate, and a graph converting the amount of signal to number of HIV-specific molecules per reaction.
Figure 4B:
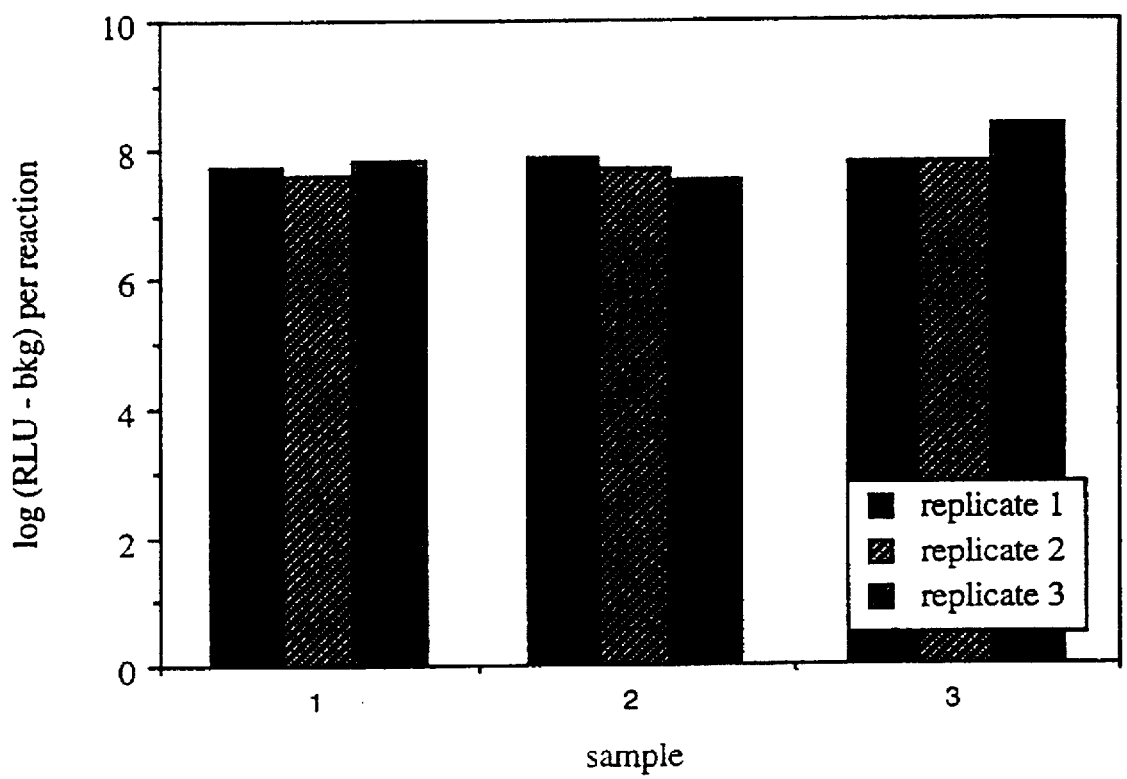
Figure 4C:
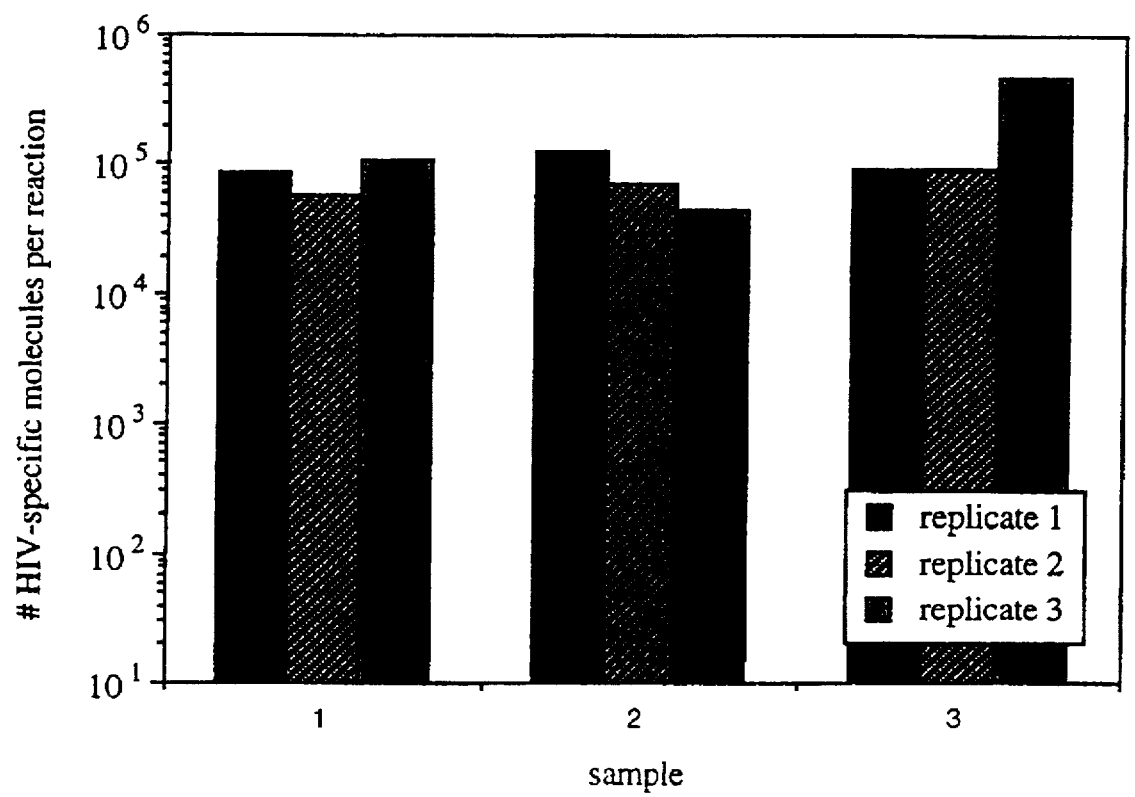
Figure 5A:
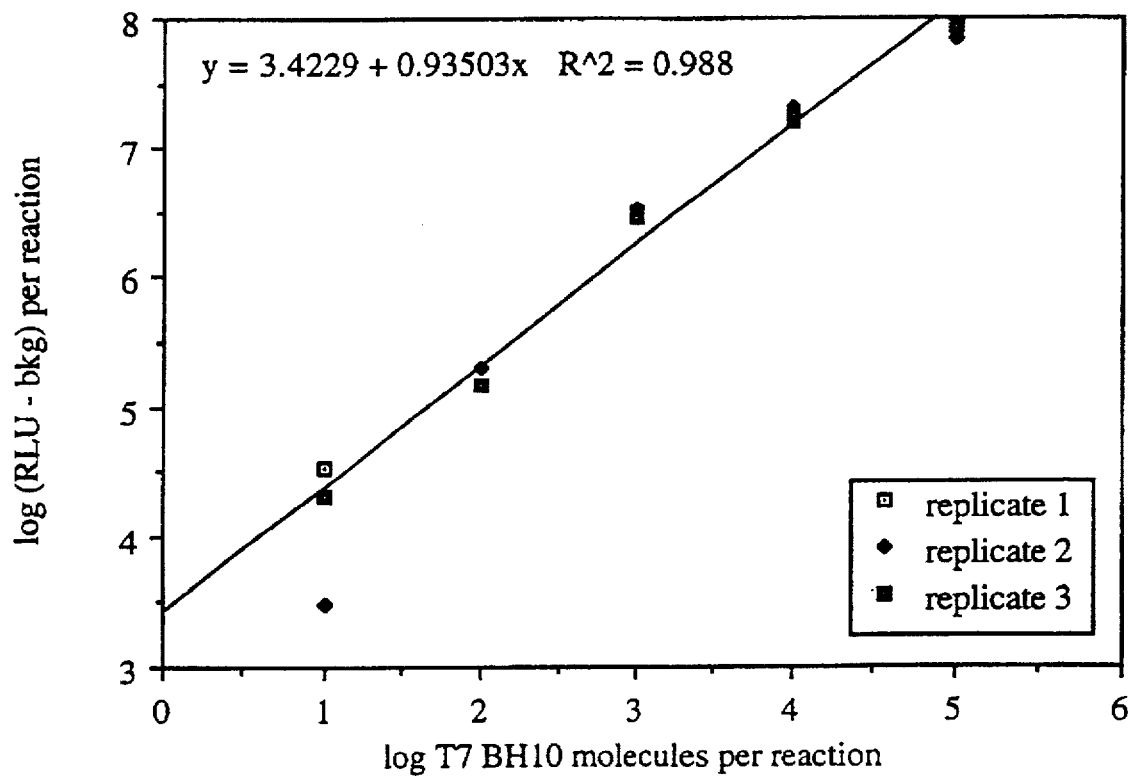
FIGS. 5A through 5C illustrate, respectively, a standard curve generated for quantitation of HIV RNA levels in vital lysates, a graph showing the amount of signal obtained in each of three experiments performed in triplicate, and a graph converting the amount of signal to number of HIV-specific molecules per reaction. Viral lysates were diluted ten-fold prior to amplification.
Figure 5B:
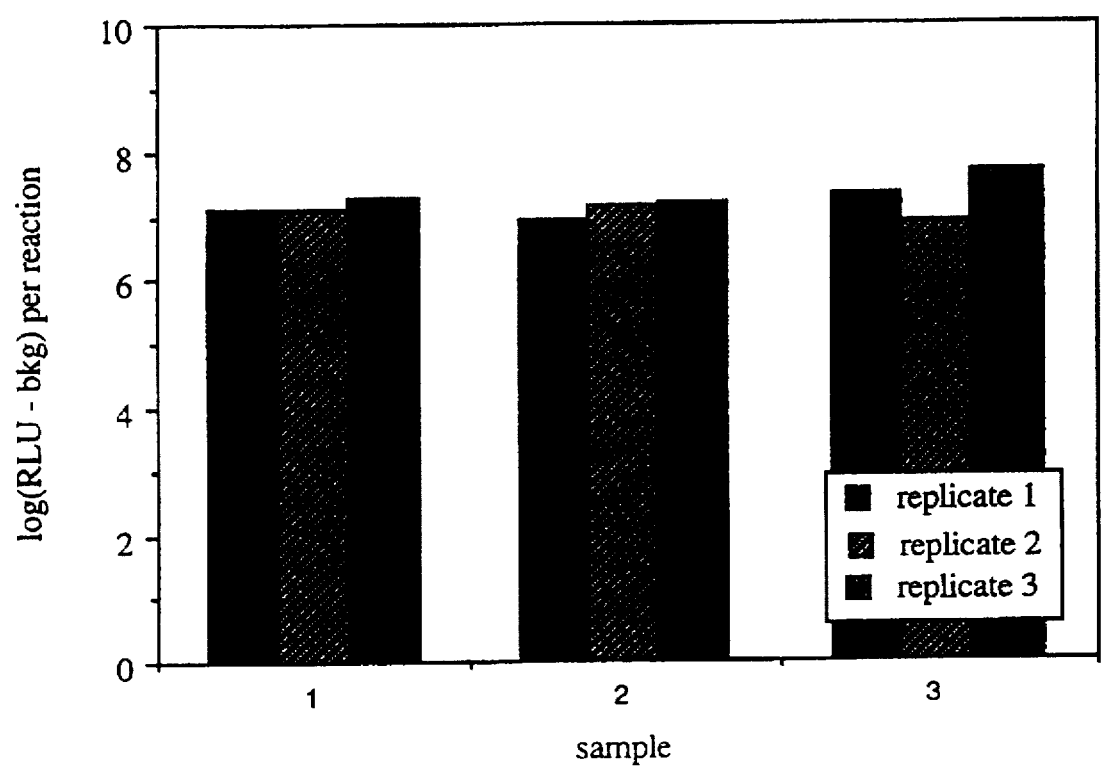
Figure 5C:
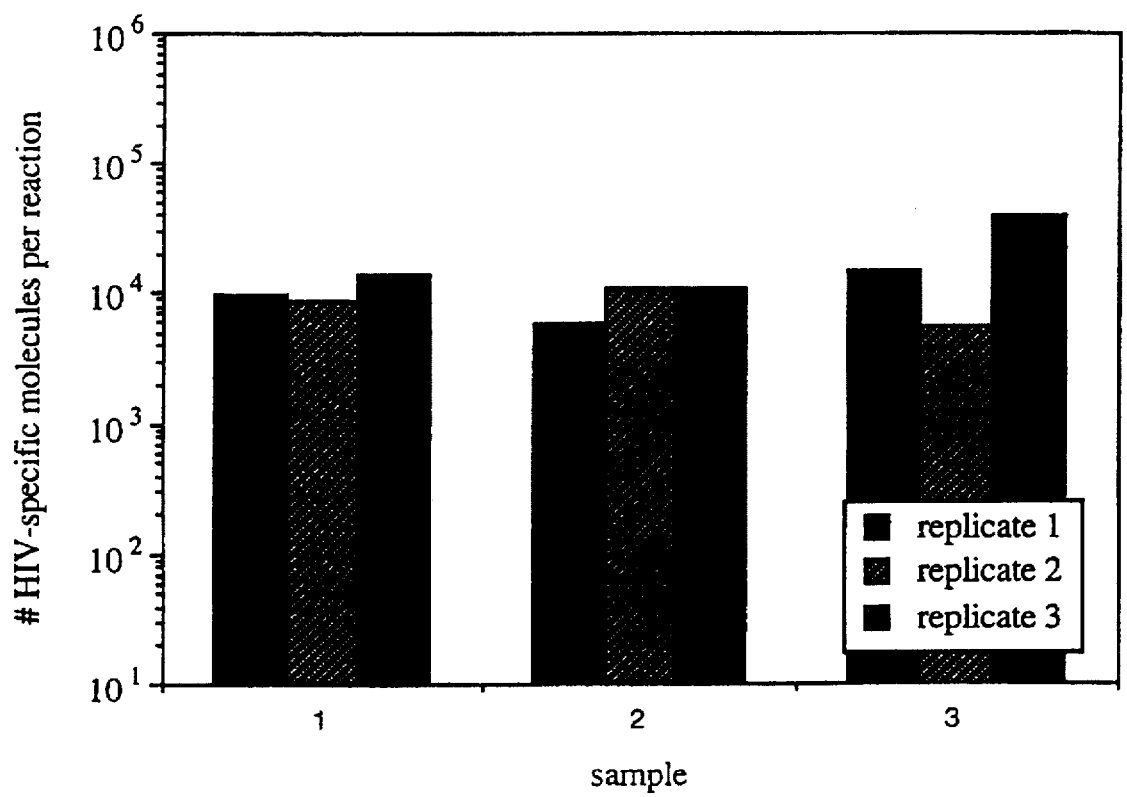
Figure 6A:
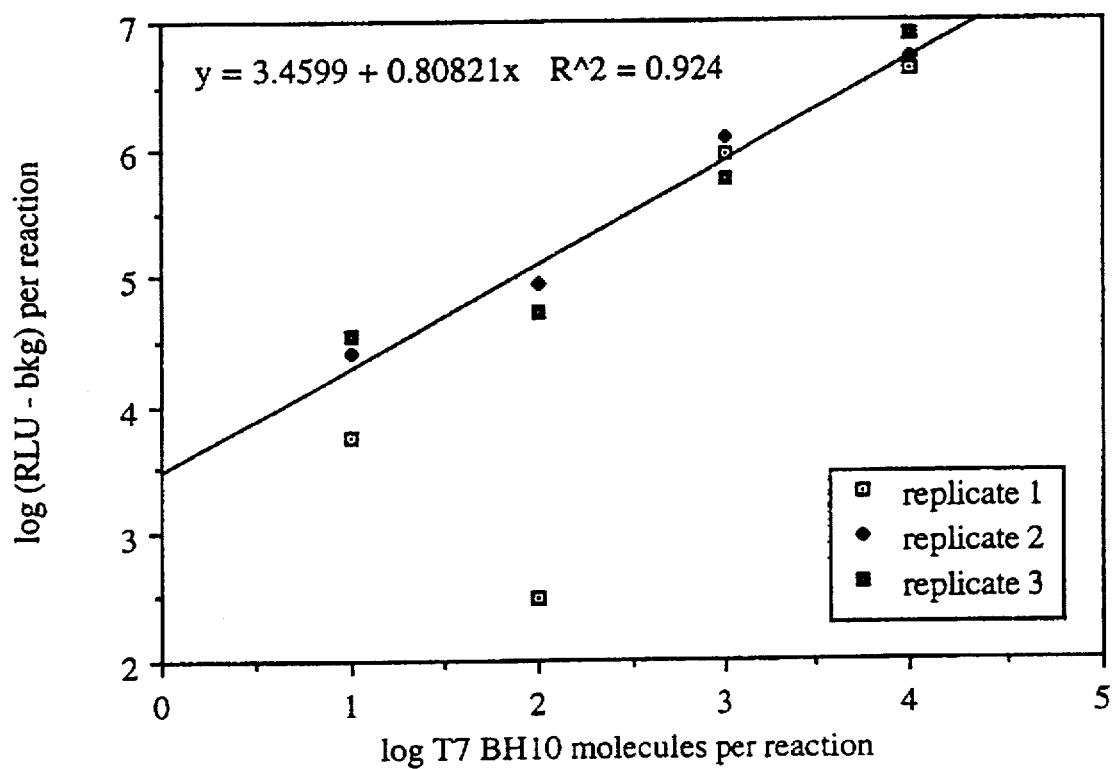
FIGS. 6A through 6C illustrate, respectively, a standard curve generated for quantitation of HIV RNA levels in vital lysates, a graph showing the amount of signal obtained in each of three experiments performed in triplicate, and a graph converting the amount of signal to number of HIV-specific molecules per reaction. Viral lysates were diluted one hundred-fold prior to amplification.
Figure 6B:
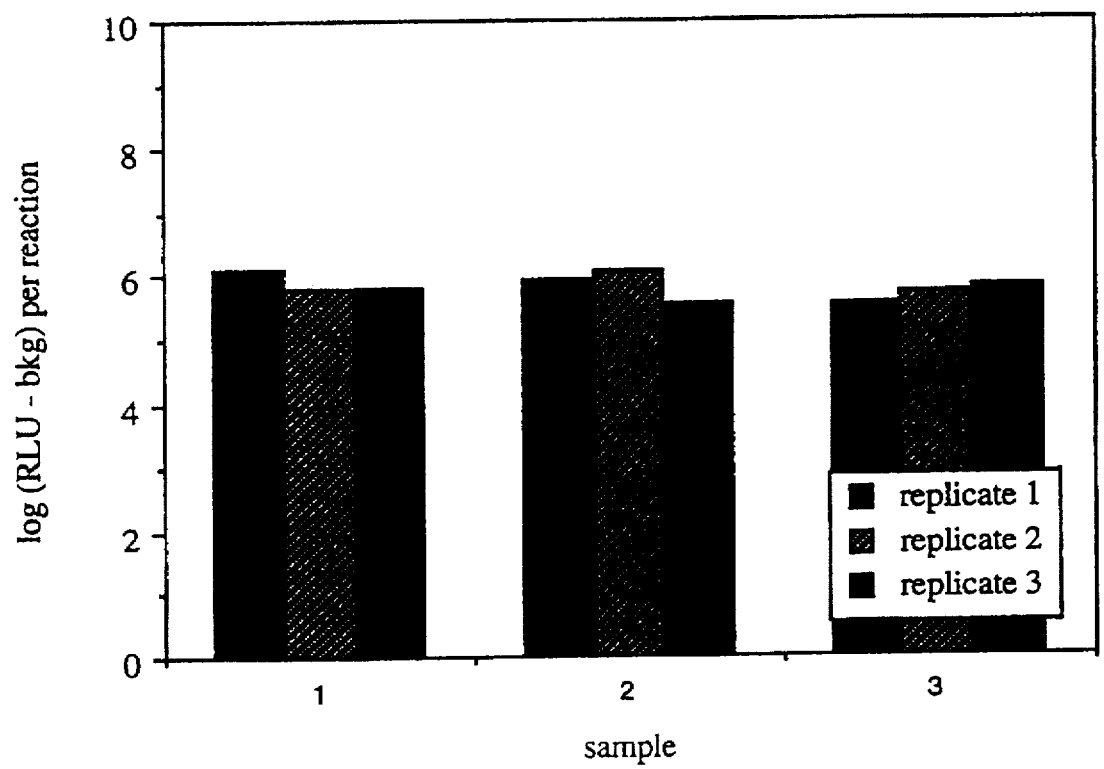
Figure 6C:
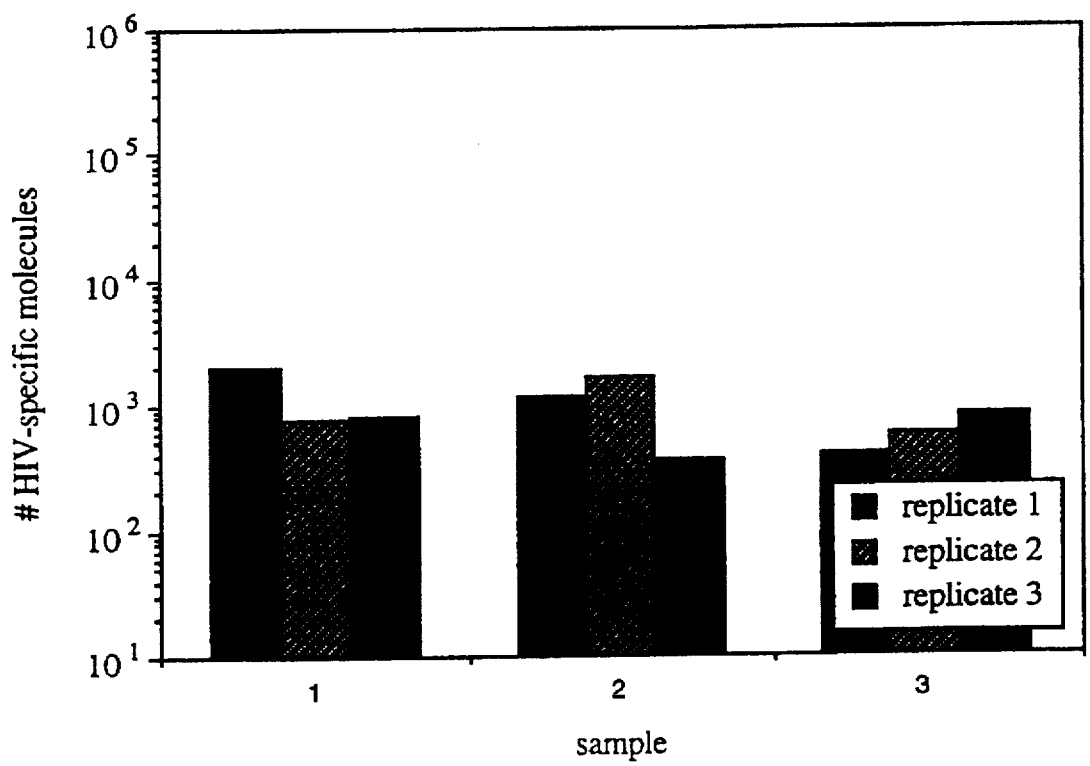
Figure 7A:
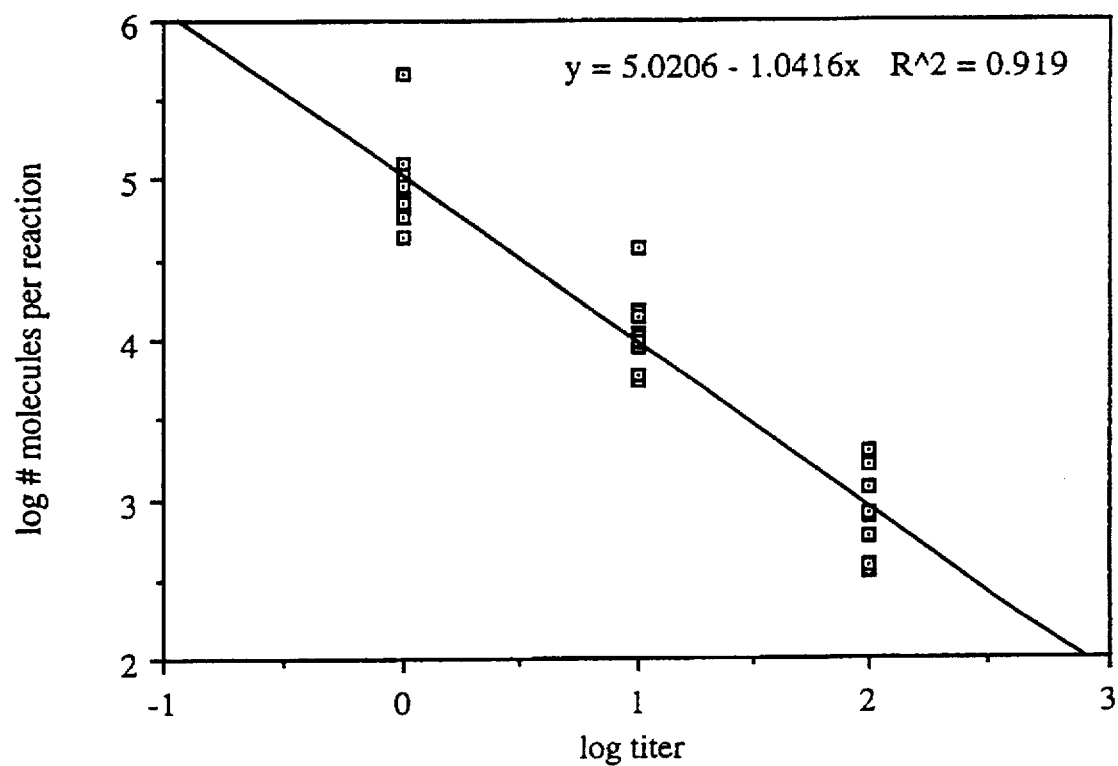
FIGS. 7A and 7B summarize the precision of the three experiments illustrated in FIGS. 4, 5 and 6.
Figure 7B:
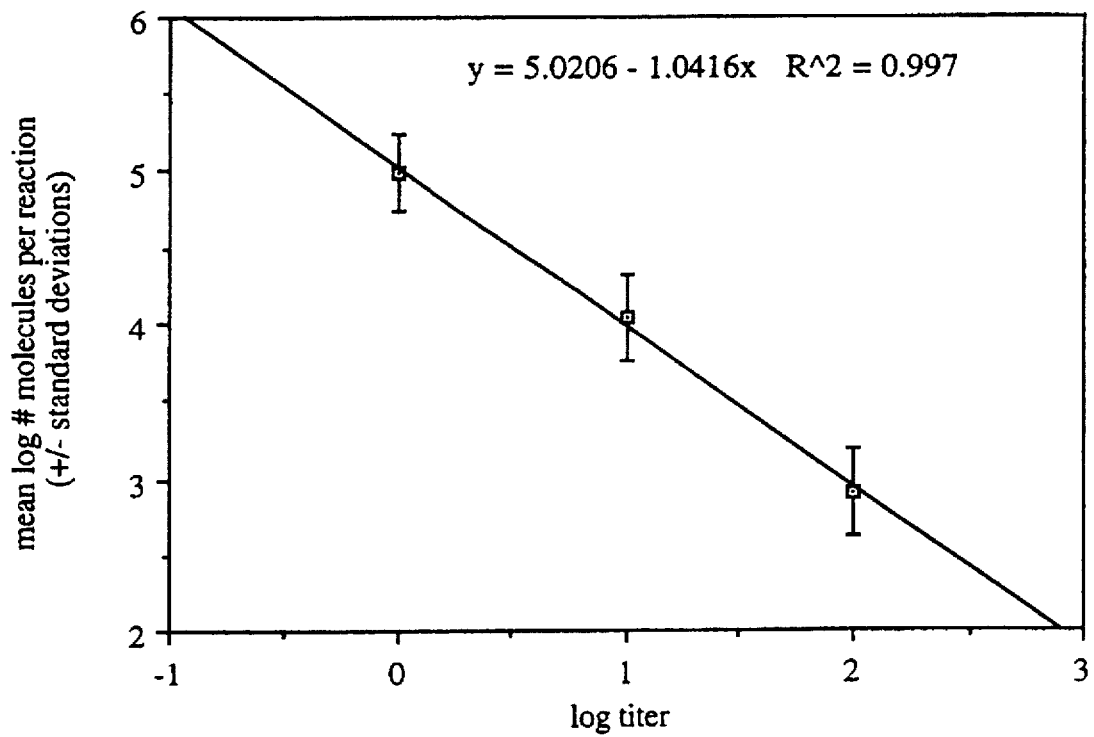

The amplification reaction was conducted as in Example 2. An external standard curve was generated using BH10 RNA for each dilution. The poly-dT selected RNA from each lysate sample and the BH10 RNA samples were all amplified in triplicate reactions. Samples representing each dilution (and their standard curves) were amplified and assayed on separate days. Results are shown in FIGS. 4, 5 and 6. The data are summarized in FIG. 7A and 7B, and below.

| EXPERIMENT | DILUTION | NUMBER OF MOLECULES PER REACTION | NUMBER OF MOLECULES PER REACTION (TIMES DILUTION FACTOR) |
|---|---|---|---|
| 1 | none | 97,600 | 97,600 |
| 2 | 10-fold | 11,000 | 110,000 |
| 3 | 100-fold | 805 | 80,500 |

The mean number of molecules detected at the three dilutions was 96,000 molecules per 50 μL of undiluted poly dT-selected HIV viral lysate. The standard deviation of the averaged different dilutions of HIV lysate unknown was 14,800 molecules in 50 μL of undiluted poly dT-selected HIV viral lysate. The coefficient of variation for the three dilutions was 15.4%.

As in the previous example, these results demonstrate remarkable precision between replicates. The replicate amplification reactions performed for the unknown amount of HIV RNA, yielded very little variation between experimental samples. As shown in FIGS. 4A, 5A and 6A, the three standard curves, each generated from triplicate amplifications of different target levels of the BH10 standard RNA, are remarkably consistent between replicate points on the standard curves.

Moreover, there is also remarkable consistency between the standard curves generated on each of the three days on which the experiments were performed. Both the slopes of the curves (0.863 (FIG. 4A), 0.93503 (FIG. 5A), and 0.808 (FIG. 6A)) and their y-intercepts (3.49 (FIG. 4A), 3.43 (FIG. 5A), and 3.46 (FIG. 6A)) are extremely similar despite the fact that the assays were conducted on different days.

The combined data therefore suggest that these methods can be used in conjunction with an external standard to precisely and predictably quantify pre-amplification levels of a target nucleic acid.

Example 5

This example illustrates another embodiment of the present invention. Two sets of reaction mixtures were compared in the following way. Each reaction mixture was as described in Example 1, with the following exceptions: desferoxamine was omitted from all reaction mixtures, the second reaction mixture contained 25 mM $MgCl_2$ (twice the concentration of the first reaction), and the oligonucleotide primers used in all the experiments were different from those used in the previous examples. Both sets of reaction mixtures contained an oligonucleotide primer of SEQ ID NO:2. The first reaction mixture also contained an promoter-primer having the nucleotide sequence SEQ ID NO:1 as its 3' portion and the T7 promoter sequence SEQ ID NO:9 as its 5' end. The second reaction mixture contained a promoter-primer having the nucleotide sequence SEQ ID NO:15 as its 3' end and SEQ ID NO:9 as its 5' end. The nucleotide sequences of SEQ ID NOS:1 and 15 are identical except that SEQ ID NO:15 contains a single extra target-complementary base at its 3' end. The target RNA was the same as was used in the previous examples and the indicated average number of copies was given to the tubes.

All of the amplification reactions contained 2000 units each of MMLV-RT and T7 RNA polymerase per 100 μL reaction mixture. Reactions were allowed to proceed for 60 minutes, then the reaction were terminated with the addition of a solution containing 100 fmoles of an acridinium ester-labeled probe of SEQ ID NO:14, complementary to the target-specific amplicon, and 1.9 pmol, 19.9 pmol or 99.9 pmol of an identical unlabeled probe depending on the initial amount of initial target copies present. Additionally, dilutions were made following the hybridization step of the reaction products prior to detection of the labeled hybrids. Both probe and sample dilution factors were taken into consideration when calculating amount of product obtained. Probe hybridization and detection were essentially as described in the previous examples.

Figure 8:
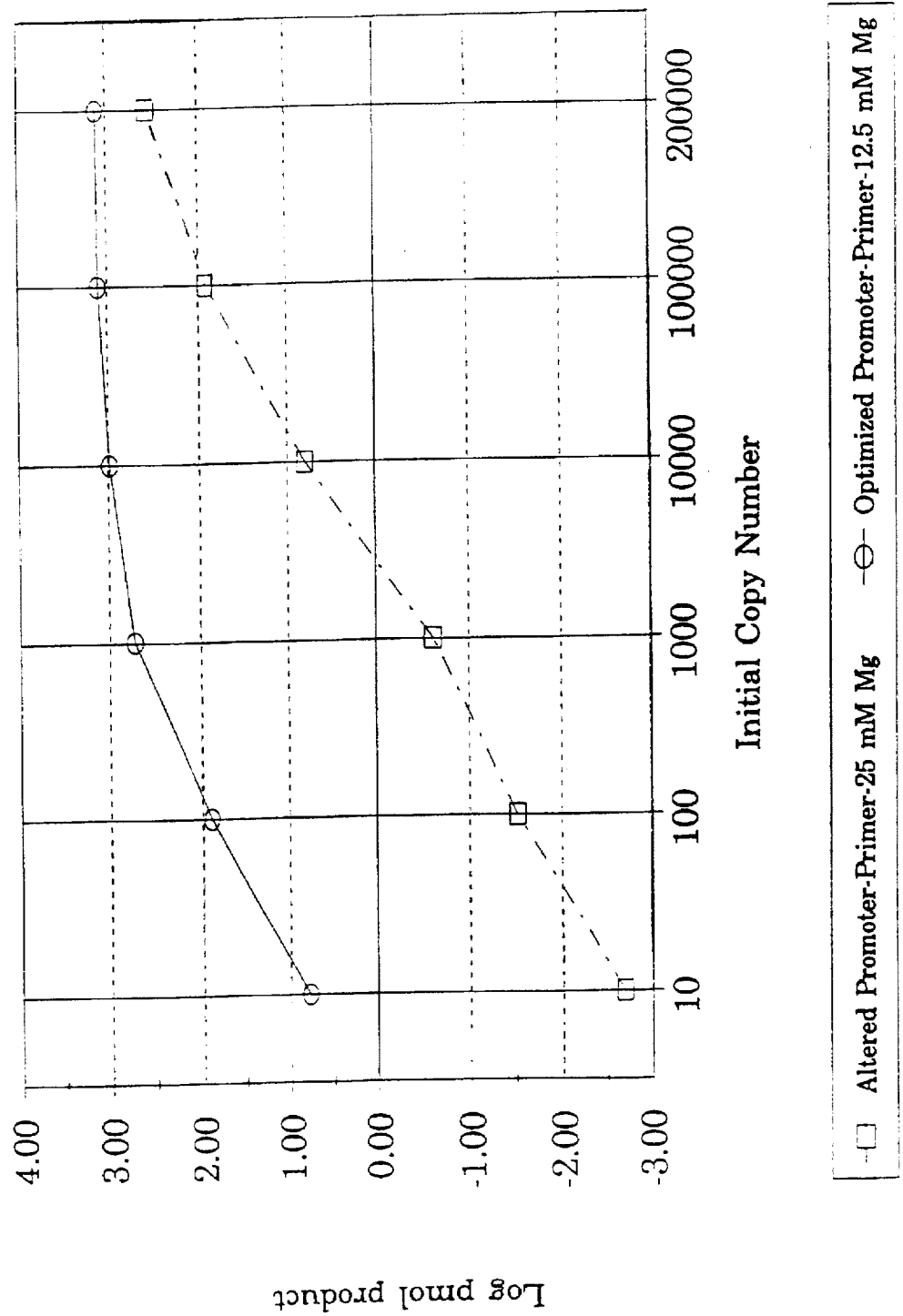
FIG. 8 is a plot of picomoles of target-specific product as a function of initial target amount. Transcription-mediated amplification was performed using two different promoter-primers and levels of magnesium.

As shown in FIG. 8, the data obtained from the first reaction mixture is similar to that seen previously when the amplification reaction was performed with 2000 units of T7 RNA polymerase; the dynamic range remains linear over one or two orders of magnitude, between about 100 and 1000 or 10,000 copies of the target sequence, with respect to the initial target concentration before the rate of the reaction begins to slow from the exponential phase. Surprisingly, in the amplification reaction containing the longer promoter-primer and 25 mM $MgCl_2$ the amount of product continues to increase exponentially as the initial target level increases exponentially; this assay shows a linear dynamic range over three to four or more orders of magnitude of target input.

This example illustrates means other than reducing the concentration of RNA polymerase in the reaction mixture may cause extension of the dynamic range of the amplification reaction. While not wishing to be bound by theory, Applicants believe that the single base addition to the promoter-primer results in a reduced ability of the primer to bind to its target, perhaps due to the secondary structure of the RNA target. Applicants have also noticed a similar effect on the the rate and dynamic range of the of the amplification reaction when the promoter sequence of the promoter-primer is truncated. This phenomenon may, therefore, be due to a reduced ability of the RNA polymerase to initiate transcription.

An increase in the $MgCl_2$ concentration has also been discovered by Applicants to have the effect of extending the reproducable dynamic range of the reaction. The extension of the dynamic range demonstrated in this figure is probably due to the combined effects of the altered promoter-primer and the raised $MgCl_2$ concentration; Applicants have observed similar effects in experiments in which only one of these two parameters has been changed.

This example also demostrates techniques for combining the strategy of extending the dynamic range of the assay with techniques for bringing the results of the amplification within the reproducable range of the detection system. In this case the latter was accomplished by a combination of using labeled probe of different specific activities and by dilution the samples before reading the results.

Example 6

In this example, the reaction mixture is the same as described for the first reaction mixture of Example 5 with the following exceptions. T7 RNA polymerase is added to the reaction mixture at a concentration of 2000 units per reaction, and the promoter-primer has a 3' target-binding portion substantially similar to SEQ ID NO:1, but having one or more base substitution causing the $T_m$ of the primer (with respect to the target nucleic acid) to decrease. Amplification, detection, and hybridization of the product target-specific amplicons are as described in Example 5.

The amplification reaction will have a reproducable dynamic range of at least three orders of magnitude, with a log/log plot of initial target copy number versus amount of target-specific product appearing similar to the conditions illustrated in FIG. 7. The initial amount of target sequence present in a sample is determined by comparision of the amount of target-specific amplicon produced in an amplification reaction conducted under these conditions with a standard curve generated under substantially identical conditions using known amounts of a standard.

According to this embodiment of the invention, the primer-binding region of the promoter-primer may contain nucleotide additions, deletions or substitutions, so long as they reduce the affinity of the primer for the primer-binding region of the target sequence, thus resulting in a submaximal promoter-primer.

Example 7

Amplification is conducted as in Example 6, except as follows. The 5' promoter portion of the promoter-primer is constructed with a reduced affinity for RNA polymerase under the amplification reaction conditions. Such submaximal promoter sequences may have design features such as a truncated promoter sequence or a promoter sequence having base substitutions as compared to a highly active promoter sequence. Amplification using at least one such promoter-primer will result in a submaximal rate of amplification and reduced amounts of product per unit time for each input level of target sequence, similar to that seen with reduced amounts of RNA polymerase in the Examples above.

The result of quantitative amplification with such a promoter-primer would be substantially similar to that under submaximal concentrations of RNA polymerase, and would be predicted by one of skill in the art, given the present disclosure, to yield an reproducable dynamic range similar to that seen in the preceding examples.

Promoter-primer modifications may include a combination of altered promoter sequences and primer binding sequences as described in this and the preceeding example. The result of such promoter-primer designs will be a reduction in the rate of the amplification reaction and an increase in the dynamic range of the amplification reaction.

Example 8

Reagents and Amplification Procedure

In Examples 9 through 12, a DNA target nucleic acid was amplified and the relationship of input target nucleic acid to target-specific amplicon product observed using the methods of the present invention. A plasmid was constructed having a double-stranded DNA insert comprising a segment of 1574 base pairs derived from the Hepatitis B virus (HBV) serotype adw genome. Plasmid construction was performed using cloning techniques well known in the art; See e.g., Sambrook et al., *Molecular Cloning: A Laboratory Manual* (2d ed. Cold Spring Harbor Laboratory Press, 1989). The HBV insert had an Xba I site at one end and a Bst EII site at the other end. A second plasmid was constructed having an insert identical to the first except for a 26 base segment in which the two clones differed in nucleotide sequence; the second insert was created using synthetic oligonucleotides to introduce site-directed substitutions into the HBV sequence.

The DNA targets were purified double-stranded restriction fragments containing the wild-type and mutant HBV inserts from the plasmids described above. Stock solutions of each purified DNA fragment were stored in a buffer containing 0.15 M NaCl, 10 mM imidazole, 10 mM glutamic acid (pH 6.8), 230 µg/mL bovine serum albumin, 5 µg/mL calf thymus DNA, 0.80% (v/v) TRITON X-102, 1.3 mM methyl paraben and 0.6 mM propyl paraben. Final dilutions were made in the same buffer or in HBV-negative human serum. The levels of each DNA fragment (target and standard) ranged from 100 copies to 10 million copies per 20 µL.

Reactions were established in 12×75 mm polypropylene test tubes as follows. Each tube received 20 µL of a solution containing 0.15 N KOH, 17.5 mM EGTA, 1.5 µM of a promoter-primer containing a 5' portion of SEQ ID NO:14 and primer binding region of SEQ ID NO:15, 1.5 µM of a primer of SEQ ID NO:16, 25 mM imidazole, 25 mM glutamic acid, 0.025% (v/v) phenol red, 0.65 mM methyl paraben, 0.28 mM propyl paraben. Each reaction mixture was layered with 200 µL of silicone oil. The appropriate amount of DNA to be amplified in a volume of 20 µL was then added to each reaction.

The DNA was denatured by incubation at 97° C. for 5 minutes, then cooled at room temperature for 10 minutes. Each reaction was then given 10 µL of a Neutralization Solution containing 330 mM imidazole, 200 mM glutamic acid (pH 7.0), 1.3 mM methyl paraben and 0.6 mM propyl paraben.

Amplification was initiated by the addition of a solution containing MMLV-RT and T7 RNA polymerase to each reaction tube. Either a lyophilized or liquid enzyme solutions were used in the following examples.

Liquid Enzyme Solution

A lyophilized Amplification Reagent contained the following: 300 µmole imidazole, 180 µmole glutamic acid, 12 µmole spermidine, 90 µmole N-acetyl-L-cysteine, 37.5 µmole rATP, 15 µmole rCTP, 37.5 µmole rGTP, 15 µmole rUTP, 1.2 µmole each of dATP, dCTP, dGTP, dTTP, 0.15 g PVP-40. This was reconstituted with 3.0 mL of a Reconstitution Buffer consisting of 41.6 mM $MgCl_2$, 1 mM zinc acetate, 0.01% (v/v) TRITON X-100, 1.3 mM methyl paraben, 0.6 mM propyl paraben. Unless otherwise indicated this buffer also contained 10% (v/v) glycerol. The final pH of this solution was 6.8.

Stock solutions of MMLV-RT contained the enzyme at a concentration of 900 units per microliter in a solution containing 50% (v/v) glycerol, 20 mM Tris HCl (pH 7.5), 100 mM NaCl, 0.10 mM EDTA, 0.01% (v/v) NP-40 and 1 mM dithiothreitol. Stock solutions of T7 RNA polymerase contained the enzyme at a concentration of 310 units per microliter in 50% (v/v) glycerol, 50 mM Tris HCl (pH 7.9), 100 mM NaCl, 0.10 mM EDTA, 0.10% (v/v) TRITON X-100 and 1 mM dithiothreitol. Two microliters of each stock solution was added to 50 µl of the reconstituted solution for each amplification reaction.

Lyophilized Enzyme Preparation

A lyophilized enzyme preparation contained: 110,000 enzyme units of MMLV-RT, 110,000 enzyme units of T7 RNA polymerase, 6.05 µmole HEPES buffer (pH 7.5), 1.5 µmole N-acetyl-L-cysteine, 0.03 µmole EDTA, 0.03 µmole zinc acetate, 30.3 µmole NaCl, 60.5 µmole trehalose and 0.55 mg equivalents TRITON X-100. This was dissolved in 2.75 mL of reconstituted Amplification Reagent.

Amplification and Detection

Fifty microliters of either liquid or lyophilized enzyme preparations, as indicated, were then added to each reaction tube and the reaction mixtures were incubated at 36° C. for 3 hours. Reactions were terminated with the addition to each reaction tube of 20 µL of a solution containing 2,500 units/mL DNase I (RNase free), 20 mM sodium acetate (pH 6.5), 100 µg/mL bovine serum albumin, 10% (v/v) glycerol, 0.01% (v/v) TRITON X-100, 25 mM calcium chloride, 1 mM $MgCl$, 0.10 mM phenylmethylsulfonyl fluoride, 1.3 mM methyl paraben and 0.6 mM propyl paraben. Tubes were then incubated for 10 minutes at 36° C. Hybridization and detection were carried out as described in previous examples.

Example 9

This example demonstrates the effect of lowering the nucleotide concentrations on the relationship between target input and target-specific amplicon product of transcription-mediated amplification. In this example, three final deoxynucleotide concentrations were evaluated: 0.20 mM each dATP, dCTP, dGTP, & dTTP (as described in Example 8); 2.0 mM each dATP, dCTP, dGTP, & dTTP; and 0.05 mM each dATP, dCTP, dGTP, & dTTP. At each dNTP level, two ribonucleotide concentrations were used. The low ribonucleotide concentration was 0.05 mM each rATP, rCTP, rGTP, & rUTP. The high ribonucleotide level was 2.0 mM each rNTP with 0.05 mM and 2.0 mM dNTPs, or 1.0 mM rNTPs with the 0.20 mM dNTPs. Amplification reactions were otherwise as described in Example 8.

Figure 9:
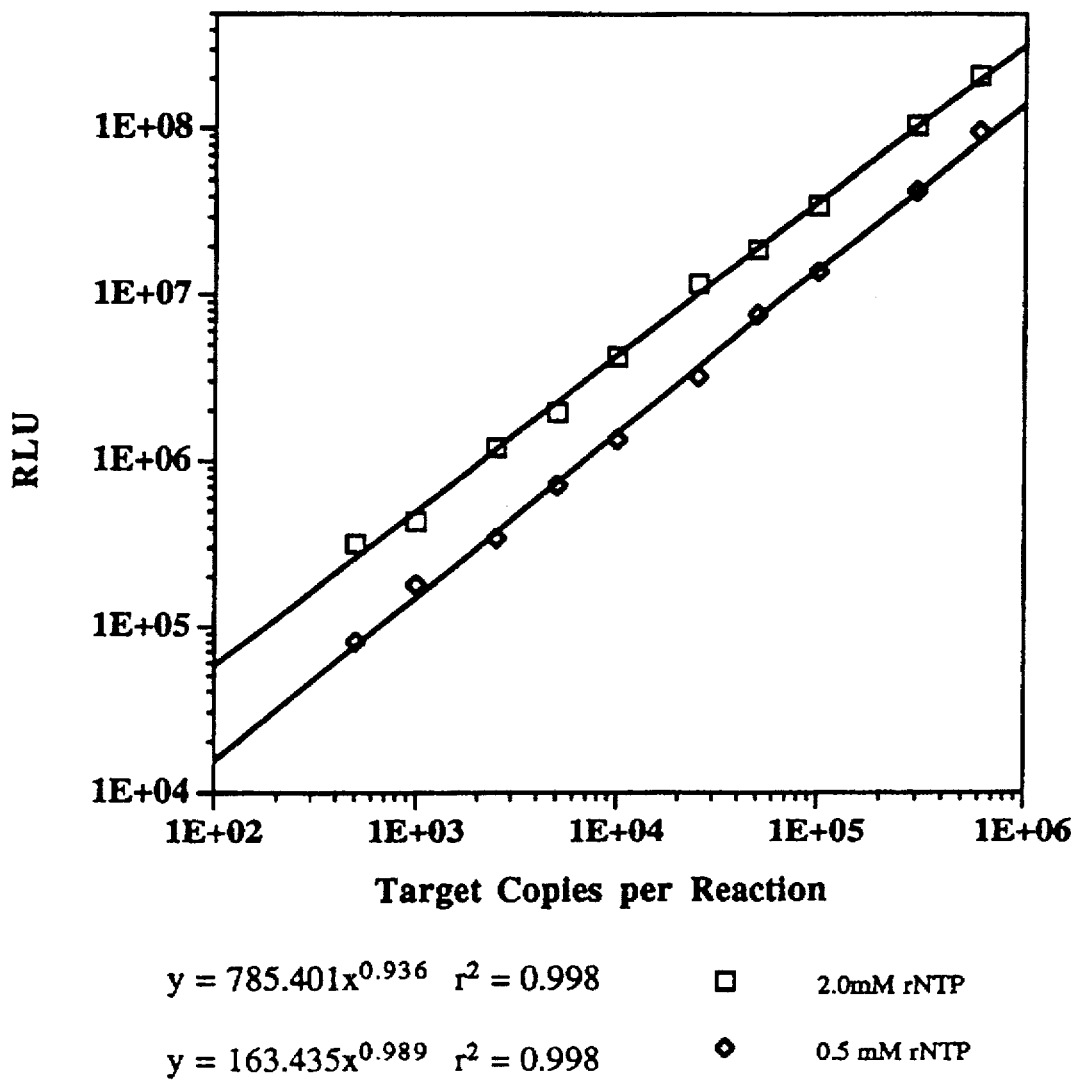
FIG. 9 shows the relationship between signal produced and initial target level when amplification is conducted at 0.05 mM each dNTP and rNTP levels are varied.
Figure 10:
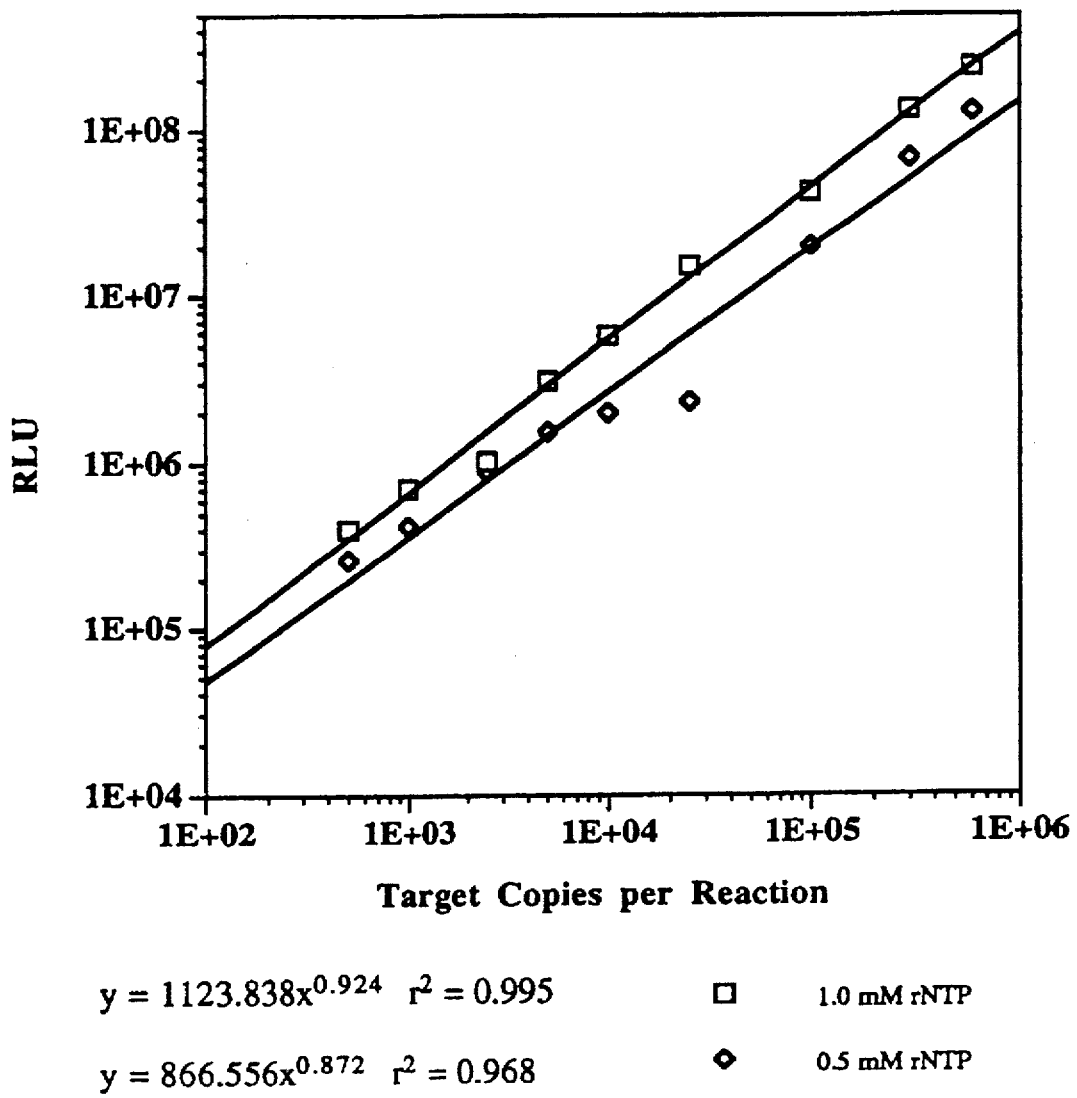
FIG. 10 shows the relationship between signal produced and initial target level when amplification is conducted at 0.2 mM each dNTP and rNTP levels are varied.
Figure 11:
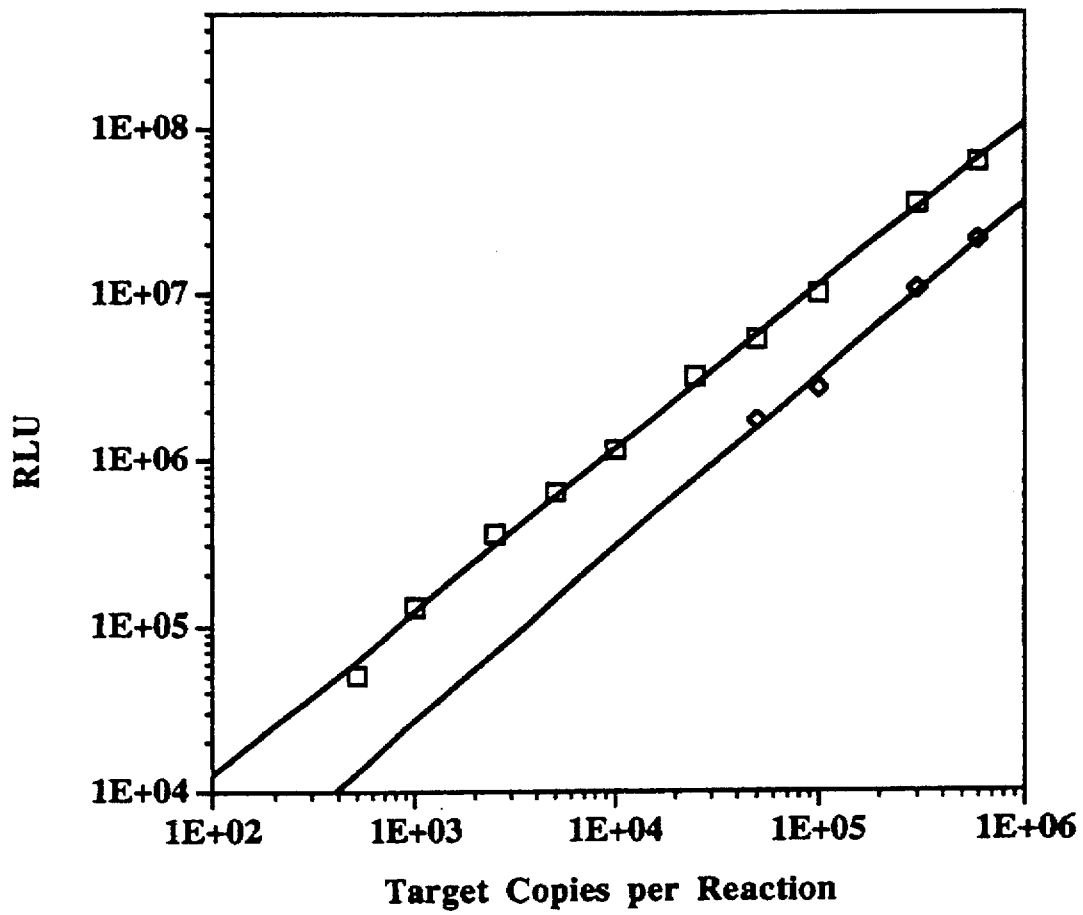
FIG. 11 shows the relationship between signal produced and initial target level when amplification is conducted at 2.0 mM each dNTP and rNTP levels are varied.

The target DNA, described in Example 8, was added to human serum as described above at target inputs ranging from 500 to 600,000 copies per reaction. The target DNA was denatured and reactions were amplified using the liquid enzyme preparation. The amplification step was conducted for two hours rather than the three hours described above. Serial dilutions of the terminated reaction mixtures were made. Hybridization and detection were as described in Example 8 and the previous examples. The total signal from each reaction was calculated by multiplying the RLUs obtained with the diluted samples by the appropriate dilution factors. Results are shown in FIGS. 9, 10 and 11.

As the data indicate, at each dNTP concentration there was a proportional relationship between the amount of signal (target-specific amplicon produced) and the amount of target input. The reactions containing either 0.05 mM (FIG. 9) or 0.20 mM dNTP (FIG. 10) showed similar curves at the higher levels of rNTPs. The reactions conducted with 2 mM dNTPs (FIG. 11) showed a similar proportional relationship but had a consistently lower yield (about 0.5 logs) than those illustrated in FIGS. 9 and 10. At all dNTP levels, a lower ribonucleotide concentration resulted in a lower signal response.

These results demonstrate that a reproducably proportional relationship exists between target input levels and target-specific product levels in the transcription-mediated amplification of DNA. The data also demonstrate that the amount of amplified product can be adjusted by changing the deoxynucleotide and/or ribonucleotide concentrations in the reactions. Finally, altering nucleotide concentrations did not appear to change the slope of the signal response.

Example 10

In this example, a target nucleic acid and a standard nucleic acid were coamplified in the same reaction mixture, using a single primer pair. Target and standard nucleic acids were those described in Example 9. The target-specific amplicon expected from this amplification had a nucleotide sequence SEQ ID NO:17. The expected standard-specific amplicon had a nucleotide sequence SEQ ID NO:18. Both standard and target nucleic acids were combined at various concentrations in HBV-negative human serum and amplified under the conditions described above. The standard differs only in the sequence of the 26 base probe binding region. The liquid enzyme preparation was used for these reactions. Amplification products were serially diluted prior to hybridization. Separate hybridizations were conducted on each reaction; one using a target-specific probe of SEQ ID NO:19 and the other using a standard-specific probe of SEQ ID NO:20.

Figure 12:
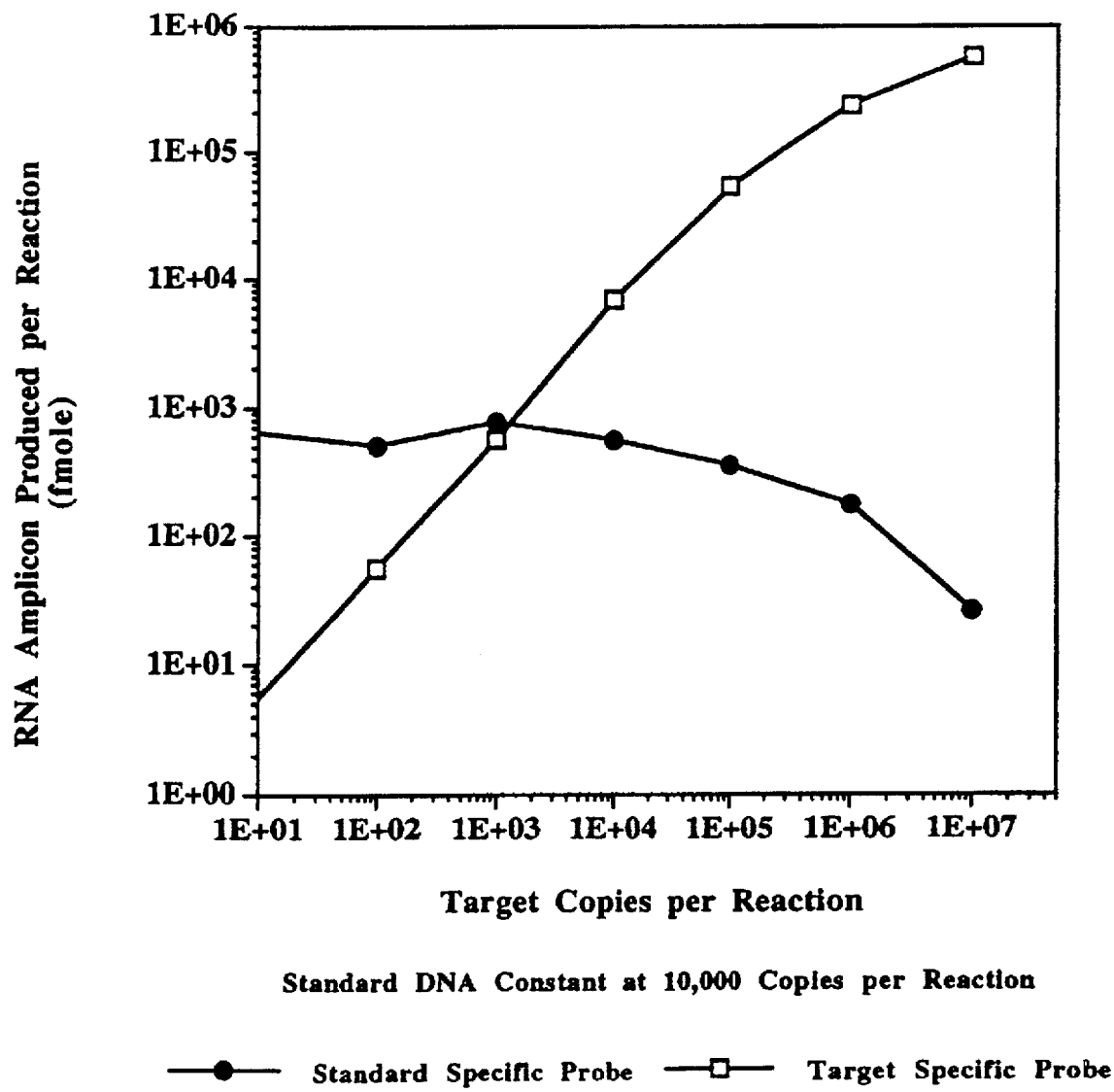
FIG. 12 shows the relationship between the amount of target and standard-specific amplicon produced in a transcription-mediated amplification system in which initial target levels are varied and initial standard levels are kept constant.
Figure 13:
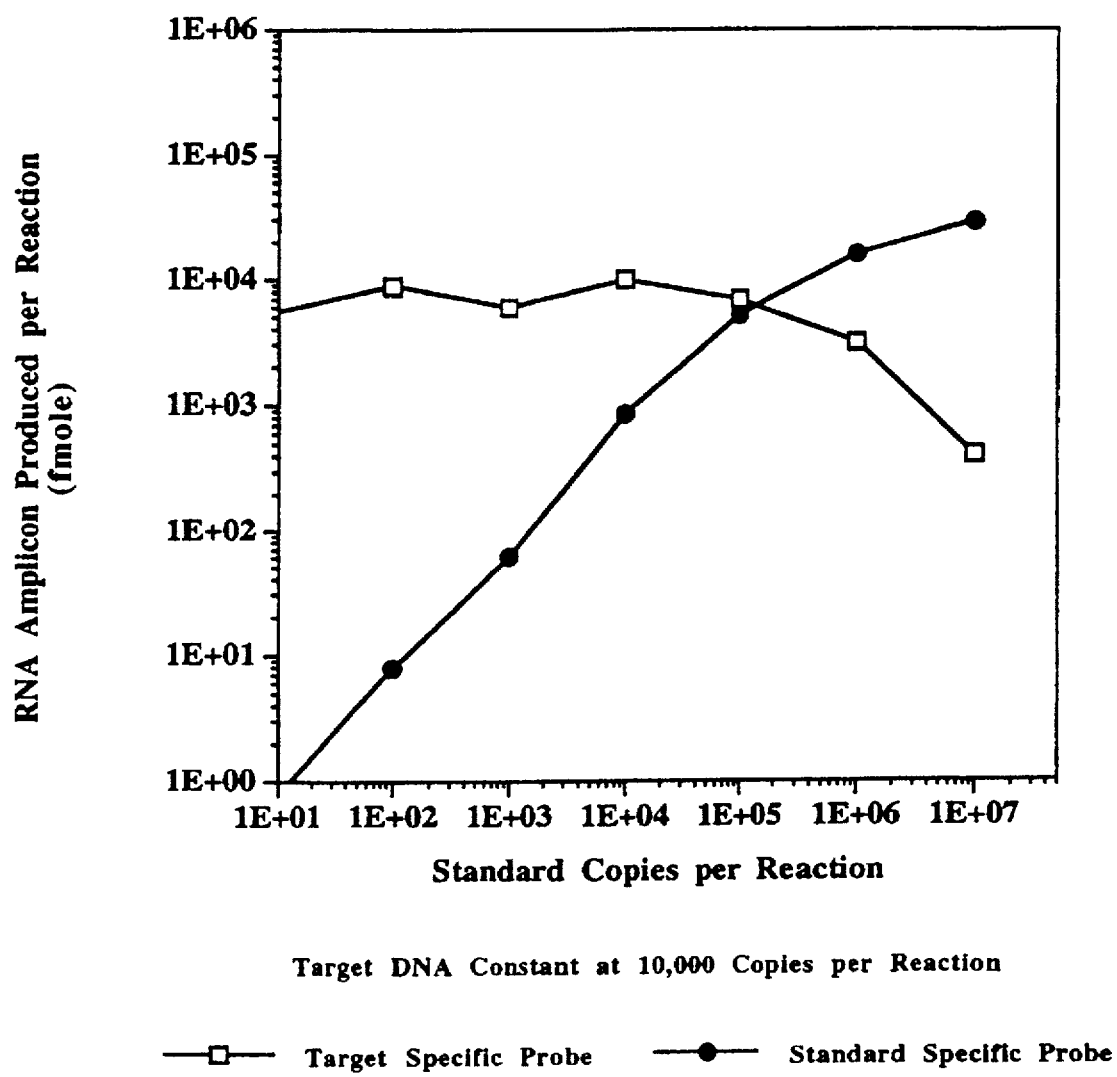
FIG. 13 shows the relationship between the amount of target and standard-specific amplicon produced in a transcription-mediated amplification system in which initial standard levels are varied and initial target levels are kept constant.

Two template combinations were compared. In the first set of reactions, the standard was supplied at a constant concentration of 10,000 copies per reaction, and the target nucleic acid concentration was varied from 100 copies to 10 million copies per reaction. In the second set of reactions, the target concentration was held constant at 10,000 copies per reaction, and the standard concentration varied from 100 to 10 million copies. Results are shown in FIGS. 12 and 13.

The data demonstrate similar trends for both sets of DNA reactant combinations. In each case, reactions in which a template concentration was increased from 100 to 1 million copies showed a proportional increase in the amount of amplicon product specific to that template, while the amplicaon specific to the template whose concentration was kept constant also remained relatively constant. When input levels were greater than 1 million copies, a deviation from linearity is observed for both target and standard. This deviation suggests that, under these conditions, the amplification system is saturated at such high DNA target levels. These results also show that the amount of amplicon produced per target input was approximately 1 log greater for the target nucleic acid than for the standard nucleic acid.

This example demonstrates that two different DNA targets can be amplified simultaneously using the transcription-mediated amplification method. Additionally, a linear relationship between nucleic acid reactant concentration and amount of amplicons produced is maintained over a 4 log dynamic range.

Example 11

Figure 14:
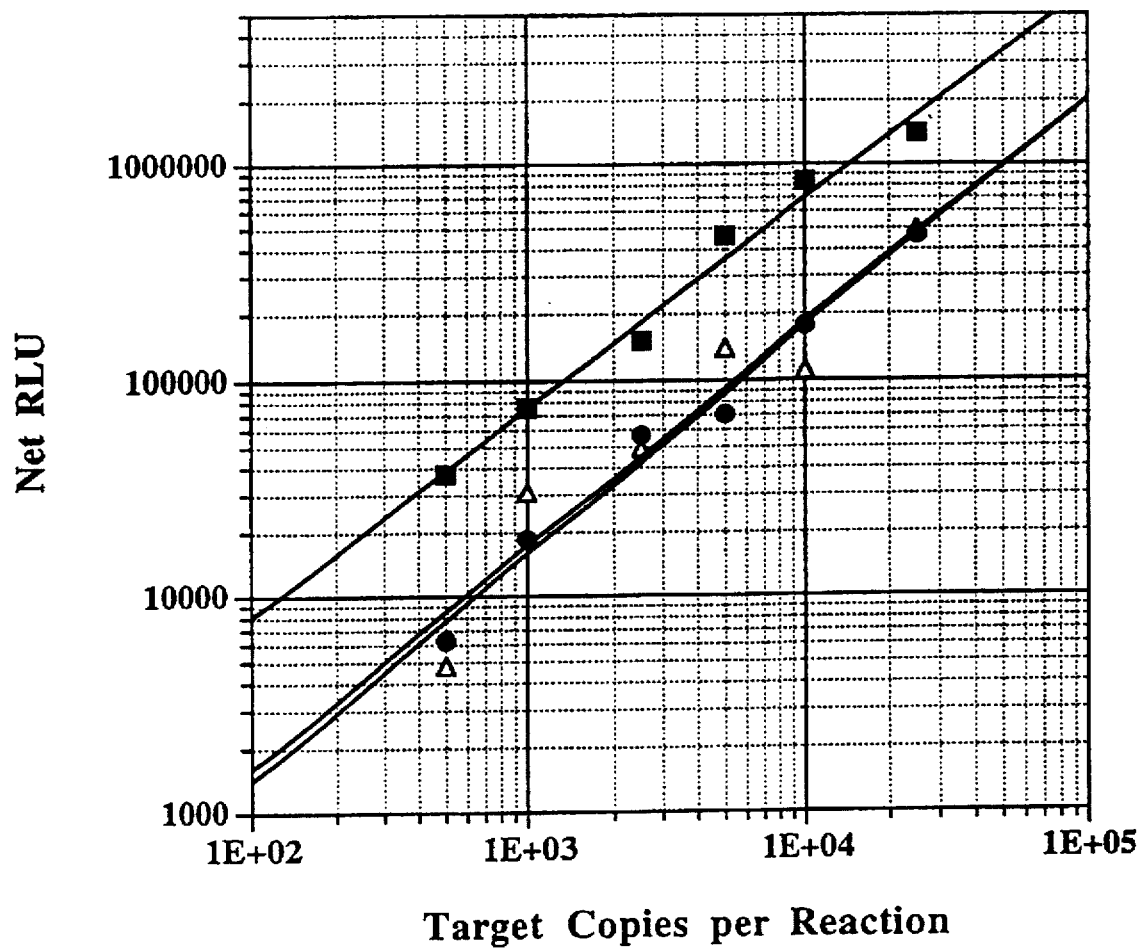
FIG. 14 shows the relationship between signal produced and initial target levels in reactions in which reverse transcriptase levels are varied.

In this experiment, amplification was conducted at different concentrations of MMLV-RT and at lowered RNA polymerase levels. Target nucleic acid concentrations of between 500 and 25,000 copies per reaction were used for each reverse transcriptase concentration. Three sets of reactions were established at reverse transcriptase concentrations of either 500, 1,000, or 2,000 enzyme units. In this experiment, lyophilized RNA polymerase was used; RNA polymerase was used at one hundred units per reaction. This solution was supplemented with the indicated amount of a liquid reverse transcriptase solution. Reactions were amplified for two hours, terminated as described above, and the reaction products detected without dilution using a target-specific probe of SEQ ID NO:19. The specific activity of the probe was adjusted to 25,000 RLU/fmole by mixing acridium ester-labeled probe with an identical unlabeled probe. Results are depicted in the graph in FIG. 14.

The data show that lowering reverse transcriptase from 2,000 enzyme units to 1,000 units results in a reduction in signal of about 0.5 log for each data point tested. Little difference was seen at all target levels between reactions having 500 or 1,000 units of reverse transcriptase. This experiment suggests that lowering the reverse transcriptase in combination with using a low T7 RNA polymerase input, can further reduce the amount of target-specific amplicon produced by the system while still maintaining the linearity of the amplification reaction.

Example 12

In this example different amounts of the target sequence were subjected to transcription-mediated amplification in two blind studies and quantitated by correlation with a standard curve generated under identical conditions. The standard curve was generated by diluting known amounts (500–600,000 copies) of the target nucleic acid into 20 µL of HBV-negative human serum. In addition, a panel of thirteen samples was prepared in the same manner but using different target inputs ranging from 0 to 600,000 copies per 20 µL.

Lyophilized enzyme reagent was used in this experiment as described above, except at 0.40 times its normal strength in each reaction mixture. Amplification was conducted as in Example 8. Reactions were amplified for two hours and the products detected by hybridization of the target-specific ampicons to a probe of SEQ ID NO:19. A labeled probe was mixed with unlabeled probe to make two probe mixtures having different specific activities. The probe mix having a high specific activity (980 RLU/fmole) was used with samples containing 500 to 25,000 copies of the target sequence. The probe mix having a low specific activity (20 RLU/fmole) was used for the target concentrations between 10,000 and 600,000 copies per reaction.

Quantification of the thirteen member panel was performed without knowledge of the actual target concentrations. Each sample in the panel was amplified in duplicate; one replicate was hybridized with the high probe specific activity and the other replicate was used with the low probe specific activity. The standard curve was generated at the same time as amplification of the sample panel.

Figure 15:
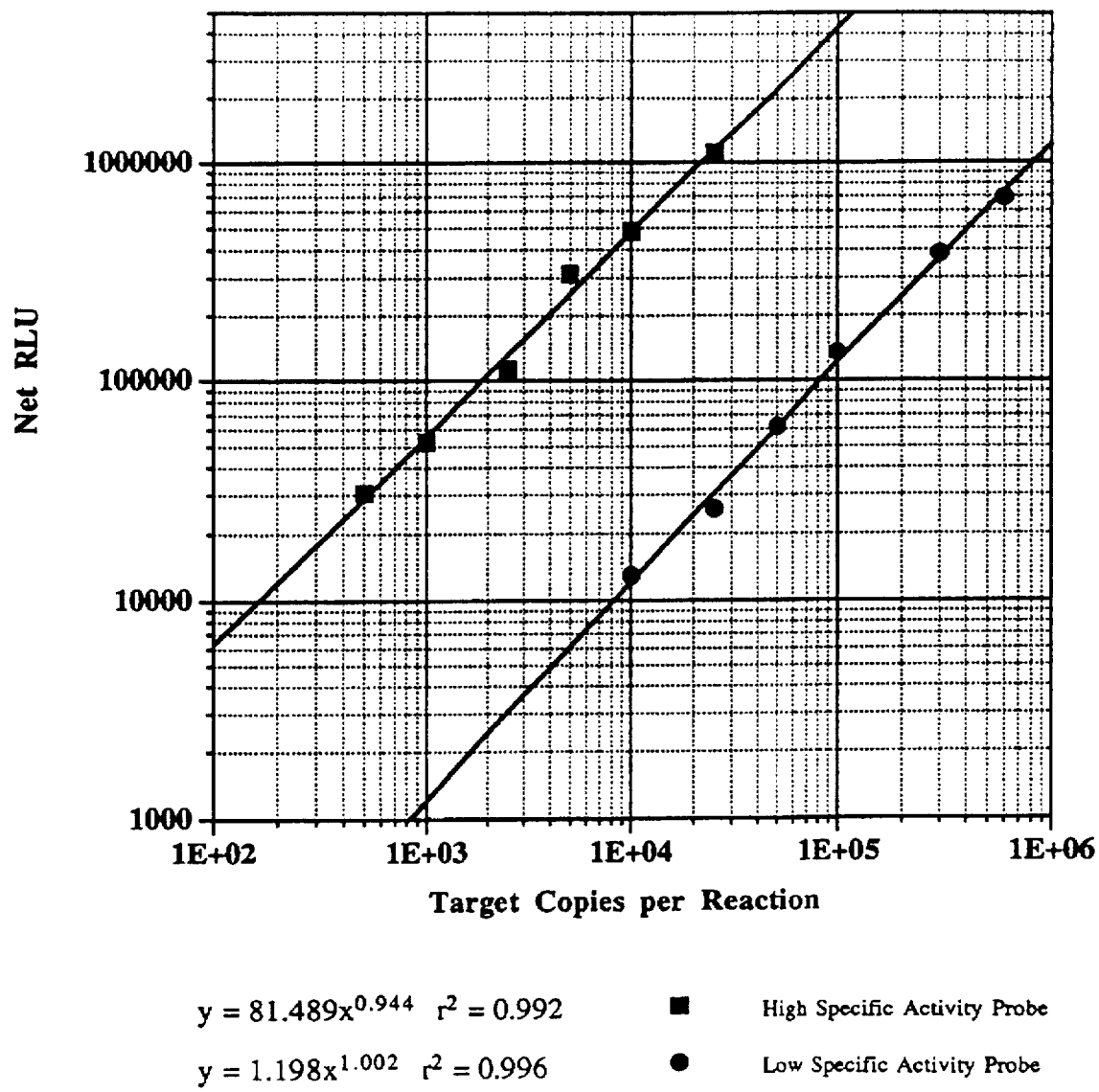
FIG. 15 shows examples of standard curves generated using low and high specific activity probe mixes.

The standard curves were plotted using both probe mixes, and the equations describing the lines were determined. An example of such a standard curve is shown in FIG. 15. The initial target levels of the samples in the "unknown" panel was estimated without knowledge of the actual target concentrations by comparing the signals to the standard curve; estimates were calculated using the equations obtained from the standard curves. Results of 2 experiments are shown in the table below and in FIG. 15.

The data show a high level of reproducablity when the unknown samples were quantitated using the standard curve generated using the external standards. Moreover, using the high and low specific activity probe mixes the need to dilute the samples in order to keep the measured signal within the linear range of the luminometer was obviated.

The DNA estimates of the unknown sample panel correlated well with the actual input. The average estimate for each sample was within 32% of input, even with samples that had initial target levels of less than 500 copies.

| Sample | Exp. I (Estimated No. of copies target) | Exp. II (estimated number of copies target) | Avg. of Exps I and II | Actual Initial Amount Target | Coefficient of Variance (C.V.) |
|---|---|---|---|---|---|
| A | 136 | 126 | 131 | 100 | 31% |
| B | 232 | 341 | 287 | 250 | 15% |
| C | 746 | 559 | 653 | 700 | −7% |
| D | 341 | 432 | 387 | 400 | −3% |
| E | 2,190 | 1,587 | 1,889 | 1,600 | 18% |
| F | 353,194 | 276,815 | 315,005 | 300,000 | 5% |
| G | 6,549 | 7,000 | 6,775 | 5,000 | 35% |
| H | 14,682 | 16,355 | 15,435 | 12,000 | 29% |
| I | 133,682 | 176,175 | 154,929 | 150,000 | 3% |
| J | 0 | 0 | 0 | 0 | not applicable |
| K | 437 | 514 | 476 | 400 | 19% |
| L | 439,643 | 478,443 | 459,043 | 400,000 | 15% |
| M | 514,312 | 467,935 | 491,124 | 600,000 | −18% |

Example 13

In this experiment, modulation of the extent of transcription-mediated amplification was investigated in sets of amplification reactions each containing different concentrations of, $MgCl_2$, a cofactor necessary for enzyme activity. The target nucleic acid was the same as that described in Example 8 and was diluted in HBV-negative human serum.

Amplification was conducted as described in Example 8 with the following differences.

The Reconstitution Buffer was made without $MgCl_2$ and zinc acetate. Zinc acetate was added to the Neutralization Reagent at a concentration of 1 mM. Various amounts of $MgCl_2$ were also added to the Neutralization Reagent to yield a range of final reaction concentrations of 9 mM, 11 mM and 13 mM per reaction. Enzymes used were contained in the lyophilized enzyme preparation described in Example 8.

For the set of amplification reactions containing 9 mM $MgCl_2$ per reaction, $5 \times 10^6$, $5 \times 10^7$, $5 \times 10^8$ and $10^9$ copies of target were added to separate reaction tubes. For the set of amplification reactions containing 11 mM $MgCl_2$ per reaction, $5 \times 10^3$, $5 \times 10^4$, $5 \times 10^5$ and $5 \times 10^6$ and $5 \times 10^7$ copies of target were added to separate reaction tubes. For the set of reactions containing 13 mM $MgCl_2$, 50, $5 \times 10^2$, $5 \times 10^3$ and $5 \times 10^4$ copies of target were added.

Hybridization was conducted as described in the previous examples without dilution of the reaction mixture or the use of probe mixes of differing specific activities.

Figure 16:
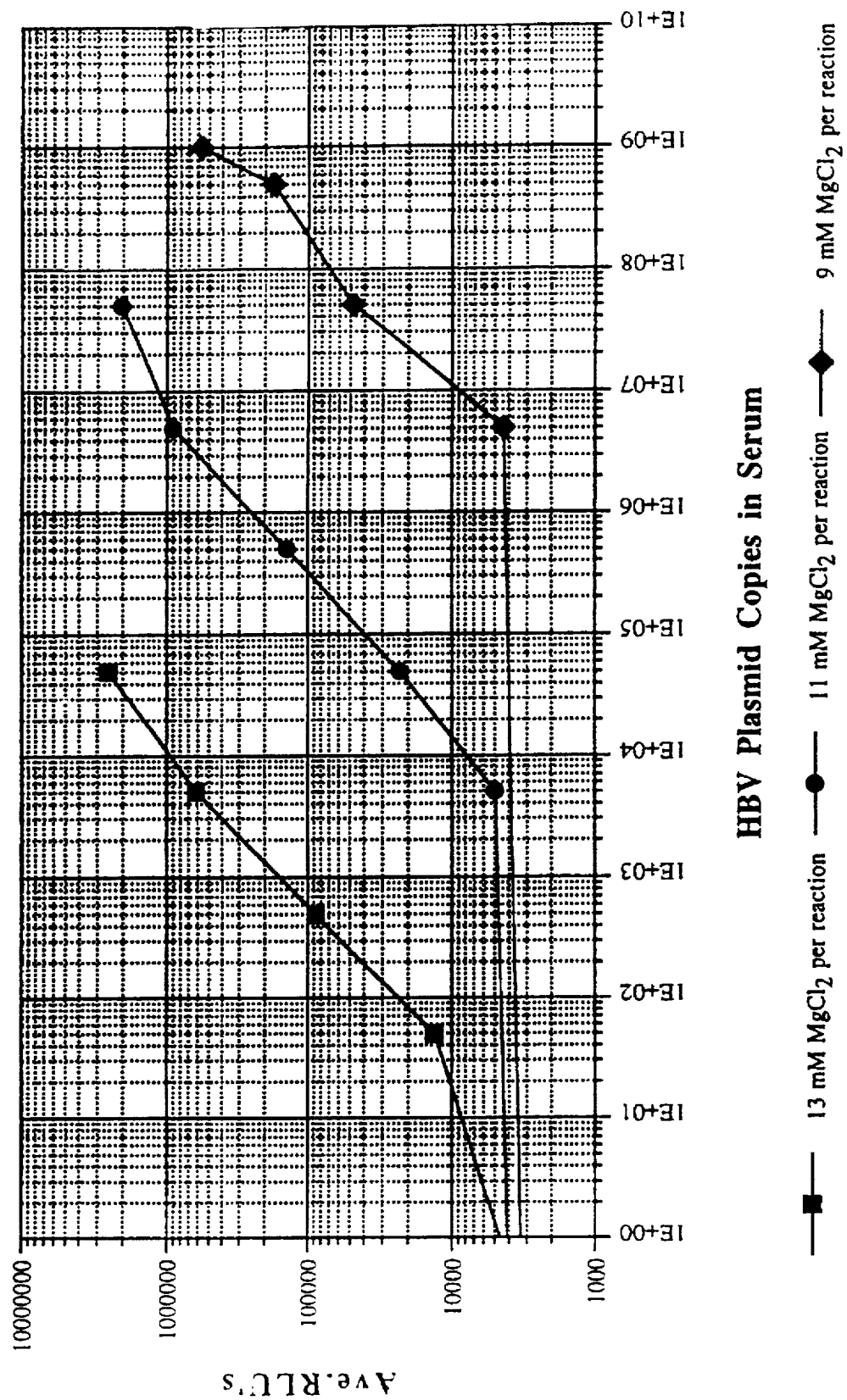
FIG. 16 shows the relationship between signal produced and initial target input levels in experiments in which magnesium levels are varied.

The results are shown in FIG. 16. As can be seen, variation of the magnesium concentration modulates the extent of the amplification reaction, allowing the proportional relationship between initial target input and target specific amplicon output to be extended over a wide range of target concentrations. By constructing standard curves similar to that shown in FIG. 16 and conducting amplification under these different magnesium concentrations the amount of target-specific amplicon can be correlated with the initial target level present before amplification.

What is claimed is:

1. A kit for determining the pre-amplification amount of a target nucleic acid sequence present in a sample from post-amplification levels of target-specific amplification products, comprising at least one vessel wherein said vessel or vessels contain:
   a) oligonucleotide primers, a retroviral reverse transcriptase, an RNA polymerase, buffers and cofactors able to cause transcription-mediated amplification when contacted with a target nucleic acid,
   b) a known amount of at least one standard nucleic acid, and
   c) at least one labeled oligonucleotide probe specific for said target nucleic acid,
   wherein said kit contains no RNAse H in addition to that provided by said reverse transcriptase.

2. The kit of claim 1 further comprising instructions for using said kit to quantify the initial amount of said target nucleic acid.

3. The kit of claim 2 wherein the amount of said RNA polymerase is no more than one half that amount required for maximal amplification of said target nucleic acid under otherwise identical reaction conditions.

4. The kit of claim 2 wherein the amount of said RNA polymerase is no more than one tenth that amount required for maximal amplification of said target nucleic acid under otherwise identical reaction conditions.

5. The kit of claim 2 wherein the amount of said RNA polymerase is not more than one twentieth that amount required for maximal amplification of said target nucleic acid under otherwise identical reaction conditions.

6. The kit of claim 2 wherein both said target nucleic acid and said standard nucleic acid have a nucleotide sequence of at least 10 bases in common.

7. The kit of claim 2 wherein both said target nucleic acid and said standard nucleic acid have a nucleotide sequence able to hybridize to said probe in common.

8. The kit of claim 1 comprising at least two vessels, one of which does not contain said oligonucleotide standard.

9. The kit of claim 2 wherein said instructions comprise directions for conducting said amplification reaction in the presence of at least two different concentrations of $Mg^{++}$.

10. A kit for determining the pre-amplification amount of a target nucleic acid sequence present in a sample from post-amplification levels of target-specific amplification products, comprising at least one vessel wherein said vessel or vessels contain:
   a) oligonucleotide primers, a retroviral reverse transcriptase, an RNA polymerase, buffers and cofactors able to cause transcription-mediated amplification when contacted with a target nucleic acid,
   b) a known amount of at least one standard nucleic acid, and
   c) at least one labeled oligonucleotide probe specific for said target nucleic acid,
   wherein said kit comprises instructions for using said kit to quantify the initial amount of said target nucleic acid and at least one promoter-primer containing a 3' modification which prevents or lessens primer extension.

11. The kit of claim 10 wherein said 3' modification is selected from the group consisting of: a ribonucleotide, a 3' deoxyribonucleotide residue, 3',2' dideoxyribonucleotide residues, a non-nucleotide linkage and an alkanediol modification.

12. The kit of claim 2 wherein said instructions comprise directions for serially diluting products of said amplification reaction prior to measuring the amount of a target-specific amplicon, if present among said products.

13. The kit of claim 2 wherein said instructions comprise directions for coamplifying said standard oligonucleotide and said target nucleic acid and correlating the amount of a target-specific amplicon produced in said amplification reaction with the amount of said standard oligonucleotide subject to said coamplification.

14. A kit for determining the pre-amplification amount of a target nucleic acid sequence present in a sample from post-amplification levels of target-specific amplification products, comprising at least one vessel wherein said vessel or vessels contain:
   a) at least one promoter-primer, a reverse transcriptase, an RNA polymerase, buffers and cofactors able to cause transcription-medicated amplification when contacted with a target nucleic acid,
   b) a known amount of at least one standard nucleic acid, and
   c) at least one labeled oligonucleotide probe specific for said target nucleic acid, wherein nucleic acids exactly complementary to said target nucleic acid and said standard nucleic acid have a nucleotide sequence able to hybridize to said probe in common.

15. The kit of claim 14 comprising at least one labeled oligonucleotide probe having a nucleotide sequence identical to at least one unlabeled oligonucleotide probe.

16. The kit of claim 15 comprising two or more vessels, each containing different ratios of said labeled and said at least one unlabeled oligonucleotide probe.

17. The kit of claim 14 further comprising instructions for using said kit to quantify the initial amount of said target nucleic acid.

18. The kit of claim 17 wherein said instructions comprise directions for conducting said transcription-mediated amplification in the presence of at least two different concentrations of $Mg^{++}$.

19. The kit of claim 14 wherein the amount of said RNA polymerase is no more than one half that amount required for maximal amplification of said target nucleic acid under otherwise identical reaction conditions.

20. The kit of claim 19 wherein the amount of said RNA polymerase is no more than one tenth that amount required for maximal amplification of said target nucleic acid under otherwise identical reaction conditions.

21. The kit of claim 20 wherein the amount of said RNA polymerase is no more than one twentieth that amount required for maximal amplification of said target nucleic acid under otherwise identical reaction conditions.

22. The kit of claim 14 comprising at least one promoter-primer containing a 3' modification which prevents or lessens primer extension.

23. The kit of claim 22 wherein said 3' modification is selected from the group consisting of at least one: ribonucleotide, 3' non-complementary deoxyribonucleotide residue, 3',2' dideoxydbonucleotide residue, non-nucleotide linkage, and alkanediol modification.

24. The kit of claim 19 comprising at least one promoter-primer containing a 3' modification which prevents or lessens primer extension.

25. The kit of claim 24 wherein said 3' modification is selected from the group consisting of at least one: ribonucleotide, 3' non-complementary deoxyribonucleotide residue, 3',2' dideoxyribonucleotide residue, non-nucleotide linkage, and alkanediol modification.

26. A kit for determining the pre-amplification mount of a target nucleic acid sequence present in a sample from post-amplification levels of target-specific amplification products, comprising at least one vessel wherein said vessel or vessels contain:
  a) oligonucleotide primers, a reverse transcriptase, an RNA polymerase, buffers and cofactors able to cause transcription-medicated amplification when contacted with a target nucleic acid,
  b) a known amount of at least one standard nucleic acid, and
  c) at least one labeled oligonucleotide probe specific for said target nucleic acid, wherein at least one of said oligonucleotide primers has a nucleotide sequence region able to hybridize with said target nucleic acid, or with nucleic acid having a nucleotide sequence region exactly complementary to a region of said target nucleic acid under amplification conditions, and wherein said primer is not perfectly complementary to said target or target-complementary nucleic acid.

27. The kit of claim 26 comprising at least one labeled oligonucleotide probe having a nucleotide sequence identical to at least one unlabeled oligonucleotide probe.

28. The kit of claim 27 comprising two or more vessels, each containing different ratios of said labeled and said at least one unlabeled oligonucleotide probe.

29. The kit of claim 26 further comprising instructions for using said kit to quantify the initial amount of said target nucleic acid.

30. The kit of claim 29 wherein said instructions comprise directions for conducting said transcription-mediated amplification in the presence of at least two different concentrations of $Mg^{++}$.

31. The kit of claim 26 wherein the amount of said RNA polymerase is no more than one half that amount required for maximal amplification of said target nucleic acid under otherwise identical reaction conditions.

32. The kit of claim 31 wherein the amount of said RNA polymerase is no more than one tenth that amount required for maximal amplification of said target nucleic acid under otherwise identical reaction conditions.

33. The kit of claim 32 wherein the amount of said RNA polymerase is no more than one twentieth that amount required for maximal amplification of said target nucleic acid under otherwise identical reaction conditions.

34. The kit of claim 26 comprising at least one promoter-primer containing a 3' modification which prevents or lessens primer extension.

35. The kit of claim 34 wherein said 3' modification is selected from the group consisting of at least one: ribonucleotide, 3' non-complementary deoxyribonucleotide residue, 3',2' dideoxyribonucleotide residue, non-nucleotide linkage, and alkanediol modification.

36. The kit of claim 29 comprising at least one promoter-primer containing a 3' modification which prevents or lessens primer extension.

37. The kit of claim 36 wherein said 3' modification is selected from the group consisting of at least one: ribonucleotide, 3' non-complementary deoxyribonucleotide residue, 3',2' dideoxyribonucleotide residue, non-nucleotide linkage, and alkanediol modification.

38. A kit for determining the pre-amplification amount of a target nucleic acid sequence present in a sample from post-amplification levels of target-specific amplification products, comprising one or more vessel comprising:
  a) a retroviral reverse transcriptase and an RNA polymerase, able to cause transcription-mediated amplification when contacted with a target nucleic acid;
  b) a standard nucleic acid;
  c) a labeled oligonucleotide probe which will hybridize to said standard nucleic acid;

wherein said retroviral reverse transcriptase is the only source of RNAse H activity contained in said kit.

39. A kit for determining the pre-amplification amount of a target nucleic acid sequence present in a sample from post-amplification levels of target-specific amplification products, comprising at least one vessel wherein said vessel or vessels contain:
  d) oligonucleotide primers, a reverse transcriptase, an RNA polymerase, buffers and cofactors able to cause transcription-medicated amplification when contacted with a target nucleic acid,
  e) a known amount of at least one standard nucleic acid,
  f) at least one labeled oligonucleotide probe specific for said target nucleic acid, and
  g) instructions for using said kit to quantify the initial amount of said target nucleic acid, wherein nucleic acids exactly complementary to said target nucleic acid and said standard nucleic acid have a nucleotide sequence able to hybridize to said probe in common.

40. A kit for determining the pre-amplification amount of a target nucleic acid sequence present in a sample from post-amplification levels of target-specific amplification products, comprising at least one vessel wherein said vessel or vessels contain:
  a) oligonucleotide primers, a reverse transcriptase, an RNA polymerase, buffers and cofactors able to cause transcription-medicated amplification when contacted with a target nucleic acid,
  b) a known amount of at least one standard nucleic acid,
  c) at least one labeled oligonucleotide probe specific for said target nucleic acid, and
  d) instructions for using said kit to quantify the initial amount of said target nucleic acid, wherein at least one of said oligonucleotide primers has a nucleotide sequence region able to hybridize with said target nucleic acid, or with nucleic acid having a nucleotide sequence region exactly complementary to a region of said target nucleic acid under amplification conditions, and wherein said primer is not perfectly complementary to said target or target-complementary nucleic acid.

41. A kit for determining the pre-amplification amount of a target nucleic acid sequence present in a sample from post-amplification levels of target-specific amplification products, comprising at least one vessel wherein said vessel or vessels contain:
  a) oligonucleotide primers, a reverse transcriptase, an RNA polymerase, buffers and cofactors able to cause transcription-medicated amplification when contacted with a target nucleic acid,
  b) a known amount of at least one standard nucleic acid,
  c) at least one labeled oligonucleotide probe specific for said target nucleic acid, and
  d) instructions for using said kit to quantify the initial amount of said target nucleic acid, and further comprising at least one unlabeled oligonucleotide probe having a nucleotide sequence identical to at least one labeled oligonucleotide probe.

42. The kit of claim 41 comprising two or more vessels each containing different ratios of said labeled and unlabeled oligonucleotide probes.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AGTTTGTATG TCTGTTGCTA TTAT        24

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

ACAAATGGCA GTATTCATCC ACA        23

( 2 ) INFORMATION FOR SEQ ID NO:3:

( i ) SEQUENCE CHARACTERISTICS:
        ( A ) LENGTH: 24 base pairs (B) TYPE: nucleic acid
(C) STRANDEDNESS: single
(D) TOPOLOGY: linear (x i) SEQUENCE DESCRIPTION: SEQ ID NO:3:

ATTCCCTACA ATCCCCAAAG TCAA 24

(2) INFORMATION FOR SEQ ID NO:4:

(i) SEQUENCE CHARACTERISTICS:
(A) LENGTH: 19 base pairs
(B) TYPE: nucleic acid
(C) STRANDEDNESS: single
(D) TOPOLOGY: linear (x i) SEQUENCE DESCRIPTION: SEQ ID NO:4:

ACCCTTCACC TTTCCAGAG 19

(2) INFORMATION FOR SEQ ID NO:5:

(i) SEQUENCE CHARACTERISTICS:
(A) LENGTH: 25 base pairs
(B) TYPE: nucleic acid
(C) STRANDEDNESS: single
(D) TOPOLOGY: linear (x i) SEQUENCE DESCRIPTION: SEQ ID NO:5:

TGCACCAGGC CAGATGAGAG AACCA 25

(2) INFORMATION FOR SEQ ID NO:6:

(i) SEQUENCE CHARACTERISTICS:
(A) LENGTH: 23 base pairs
(B) TYPE: nucleic acid
(C) STRANDEDNESS: single
(D) TOPOLOGY: linear (x i) SEQUENCE DESCRIPTION: SEQ ID NO:6:

AGATTTCTCC TACTGGGATA GGT 23

(2) INFORMATION FOR SEQ ID NO:7:

(i) SEQUENCE CHARACTERISTICS:
(A) LENGTH: 23 base pairs
(B) TYPE: nucleic acid
(C) STRANDEDNESS: single
(D) TOPOLOGY: linear (x i) SEQUENCE DESCRIPTION: SEQ ID NO:7:

ATTGGACCAG CAAGGTTTCT GTC 23

(2) INFORMATION FOR SEQ ID NO:8:

(i) SEQUENCE CHARACTERISTICS:
(A) LENGTH: 20 base pairs
(B) TYPE: nucleic acid
(C) STRANDEDNESS: single
(D) TOPOLOGY: linear (x i) SEQUENCE DESCRIPTION: SEQ ID NO:8:

AAGTGACATA GCAGGAACTA 20

(2) INFORMATION FOR SEQ ID NO:9:

(i) SEQUENCE CHARACTERISTICS:
(A) LENGTH: 26 base pairs
(B) TYPE: nucleic acid
(C) STRANDEDNESS: single ( D ) TOPOLOGY: linear ( x i ) SEQUENCE DESCRIPTION: SEQ ID NO:9:

AATTTAATAC GACTCACTAT AGGGAG  26

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CTACTATTCT TTCCCTGCA CTGTACCCC  29

( 2 ) INFORMATION FOR SEQ ID NO:11:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GTCATCCATC CTATTTGTTC CTGAAGGGTA CTAGTAG  37

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CCATCCTATT TGTTCCTGAA GGGTAC  26

( 2 ) INFORMATION FOR SEQ ID NO:13:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CCAATCCCCC CTTTTCTTTT AAAATTGTGG ATG  33

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

AATTTAATAC GACTCACTAT AGGGAGACCA CA  32

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CGAGATTGAG ATCTTCTGCG ACGCG 25

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

CACCAAATGC CCCTATCTTA TCAACACTTC CGG 33

( 2 ) INFORMATION FOR SEQ ID NO:17:

( i ) SEQUENCE CHARACTERISTICS:
        ( A ) LENGTH: 153 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GGGAGACCAC ACGAGAUUGA GAUCUUCUGC GACGCGGCGA UUGAGAUCUG CGUCUGCGAG 60

GCGAGGGAGU UCUUCUUCUA GGGGACCUGC CUCGGUCCCG UCGUCUAACA ACAGUAGUUU 120

CCGGAAGUGU UGAUAAGAUA GGGGCAUUUG GUG 153

( 2 ) INFORMATION FOR SEQ ID NO:18:

( i ) SEQUENCE CHARACTERISTICS:
        ( A ) LENGTH: 153 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GGGAGACCAC ACGAGAUUGA GAUCUUCUGC GACGCGGCGA UUGAGAUCUG CGUCUGCGAG 60

GCUGUCGGUA GGAAUUCCUA CGGCUGGUGC CUCGGUCCCG UCGUCUAACA ACAGUAGUUU 120

CCGGAAGUGU UGAUAAGAUA GGGGCAUUUG GUG 153

( 2 ) INFORMATION FOR SEQ ID NO:19:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GGTCCCCTAG AAGAAGAACT CCCTCG 26

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GGCTGTCGGT AGGAATTCCT ACGGCTGGGG 30